United States Patent
Cam et al.

(10) Patent No.: US 12,144,704 B2
(45) Date of Patent: Nov. 19, 2024

(54) ENERGY-DELIVERING ORTHODONTIC ALIGNER SYSTEMS

(71) Applicant: Align Technology, Inc., San Jose, CA (US)

(72) Inventors: Bruce Cam, San Jose, CA (US); Yaser Shanjani, Milpitas, CA (US); Jun Sato, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 553 days.

(21) Appl. No.: 16/691,141

(22) Filed: Nov. 21, 2019

(65) Prior Publication Data
US 2020/0155276 A1    May 21, 2020

Related U.S. Application Data

(60) Provisional application No. 62/770,494, filed on Nov. 21, 2018.

(51) Int. Cl.
*A61C 7/08*    (2006.01)
*A61F 7/00*    (2006.01)
(Continued)

(52) U.S. Cl.
CPC .............. *A61C 7/08* (2013.01); *A61F 7/12* (2013.01); *A61N 1/0548* (2013.01); *A61N 1/40* (2013.01);
(Continued)

(58) Field of Classification Search
CPC ...... A61C 7/08; A61F 7/12; A61F 2007/0017; A61N 1/0548; A61N 1/40; A61N 5/0603;
(Continued)

(56) References Cited

U.S. PATENT DOCUMENTS

| | | |
|---|---|---|
| 5,975,893 A | 11/1999 | Chishti et al. |
| 6,309,215 B1 | 10/2001 | Phan et al. |

(Continued)

FOREIGN PATENT DOCUMENTS

| | | | |
|---|---|---|---|
| WO | WO-2016168939 A1 * | 10/2016 | ............... A61C 7/08 |
| WO | WO-2018132912 A1 * | 7/2018 | ............. A61C 19/06 |

OTHER PUBLICATIONS

"Anirudh Agarwal, Maxillary Expansion, Aug. 13, 2016, JayPee" (Year: 2016).*

(Continued)

*Primary Examiner* — Carl H Layno
*Assistant Examiner* — Aya Ziad Bakkar
(74) *Attorney, Agent, or Firm* — Shay Glenn LLP

(57) ABSTRACT

Aligner systems and methods including a sequence of aligners having energy-delivering elements. For example, first and second aligners of the sequence of aligners may include first and second polymer shells that have shapes for applying respective first and second local forces to first and second regions of a dental arch to move one or more first teeth and one or more second teeth, respectively. The first and second aligners may also include corresponding first and second heating elements that are arranged to heat first and second target regions of the dental arch associated with moving the one or more first teeth and one or more second teeth, respectively. Heat energy from the first and second heating elements may improve an outcome of respective first and second stages of a treatment plan.

38 Claims, 12 Drawing Sheets

(51) Int. Cl.
 *A61F 7/12* (2006.01)
 *A61N 1/05* (2006.01)
 *A61N 1/40* (2006.01)
 *A61N 5/06* (2006.01)

(52) U.S. Cl.
 CPC ......... *A61N 5/0603* (2013.01); *A61N 5/0613* (2013.01); *A61F 2007/0017* (2013.01); *A61N 2005/0606* (2013.01); *A61N 2005/063* (2013.01); *A61N 2005/0662* (2013.01); *A61N 2005/0667* (2013.01)

(58) Field of Classification Search
 CPC .......... A61N 5/0613; A61N 2005/0606; A61N 2005/063; A61N 2005/0662; A61N 2005/0667
 See application file for complete search history.

(56) References Cited

U.S. PATENT DOCUMENTS

| | | |
|---|---|---|
| 6,450,807 B1 | 9/2002 | Chishti et al. |
| 6,749,414 B1 | 6/2004 | Hanson et al. |
| 6,830,450 B2 | 12/2004 | Knopp et al. |
| 7,892,474 B2 | 2/2011 | Shkolnik et al. |
| 2014/0061974 A1 | 3/2014 | Tyler |
| 2014/0265034 A1 | 9/2014 | Dudley |
| 2015/0097315 A1 | 4/2015 | DeSimone et al. |
| 2015/0097316 A1 | 4/2015 | DeSimone et al. |
| 2015/0102532 A1 | 4/2015 | DeSimone et al. |
| 2016/0081769 A1* | 3/2016 | Kimura ................. A61C 7/002 433/7 |
| 2017/0080249 A1* | 3/2017 | Brawn ................ A61N 5/0603 |
| 2018/0177570 A1* | 6/2018 | Alauddin ............... A61C 19/04 |

OTHER PUBLICATIONS

Agarwal et al., "Maxillary Expansion," Int. Journal. Pediatr. Dent, Sep.-Dec. 2010, vol. 3(3), pp. 139-146.

* cited by examiner

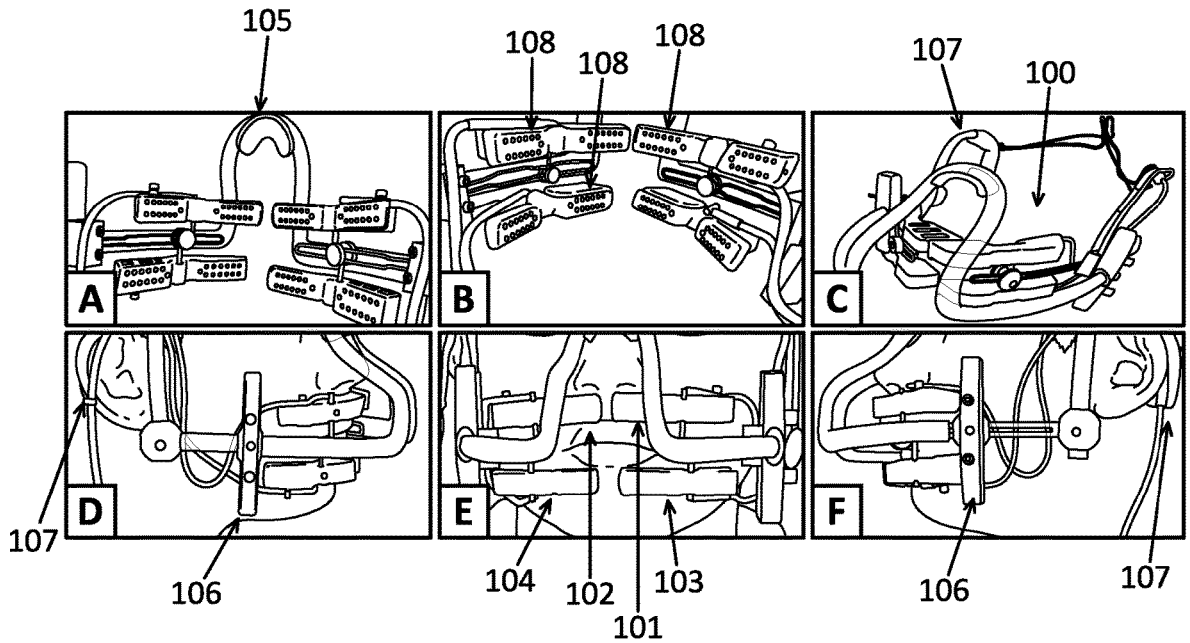
FIGS. 1A-1F
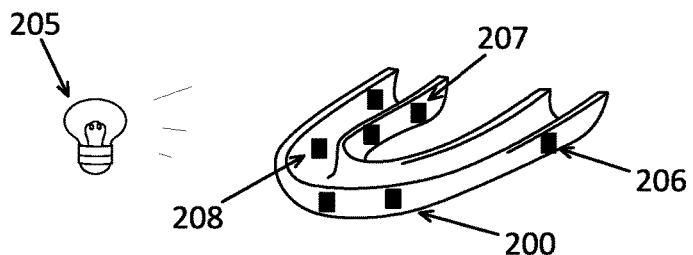
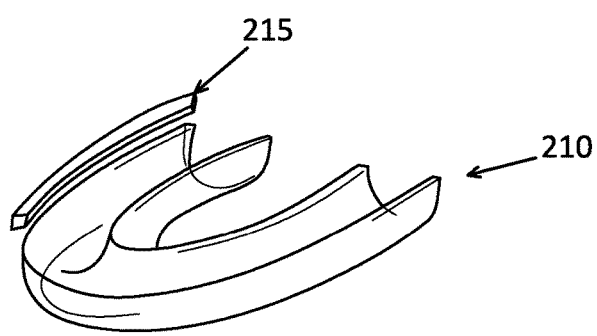
FIG. 2A ical force to move one or more teeth. For example, in some variations the appliance include a light source and an optical channel (e.g., light guide, waveguide, light-transmitting channel) between the light source and a portion of the appliance that is adapted to expose the portion of the dental arch to be modified by the current or a subsequent (immediately subsequent) appliance. For example, the optical channel may include a diffuser (e.g. diffusion film). In one example, the appliance includes an LED light source within the appliance and/or a light-input region that is connected via a light-transmitting optical channel through the appliance to a light output region that is limited to a portion of the appliance that applies a rotational and/or translational force to a specific sub-region of the dental arch (e.g., a molar, a
ENERGY-DELIVERING ORTHODONTIC ALIGNER SYSTEMS

CROSS REFERENCE TO RELATED APPLICATIONS

This application claims the benefit of U.S. Patent Application No. 62/770,494, filed Nov. 21, 2018, titled "ENERGY-DELIVERING ORTHODONTIC ALIGNERS," which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are orthodontic appliances, including in particular, aligners, that are configured to deliver energy (e.g., light and/or heat and/or electrical energy) to regions of a patient's dental arch.

BACKGROUND

An objective of orthodontics is to move a patient's teeth to positions where function and/or aesthetics are optimized. Traditionally, appliances such as braces are applied to a patient's teeth by an orthodontist or dentist and the set of braces exerts continual force on the teeth and gradually urges them toward their intended positions. Over time and with a series of clinical visits and adjustments to the braces, the orthodontist adjusts the appliances to move the teeth toward their final destination.

Alternatives to conventional orthodontic treatment with traditional affixed appliances (e.g., braces) include systems including a series of preformed aligners. In these systems, multiple, and sometimes all, of the aligners to be worn by a patient may be designed and/or fabricated before the aligners are administered to a patient and/or reposition the patient's teeth (e.g., at the outset of treatment). The design and/or planning of a customized treatment for a patient may make use of computer-based three-dimensional (3D) planning/design tools. The design of the aligners can rely on computer modeling of a series of planned successive tooth arrangements, and the individual aligners are designed to be worn over the teeth and elastically reposition the teeth to each of the planned tooth arrangements.

Once designed and/or planned, a series of preformed aligners may be fabricated from a material that, alone or in combination with attachments, imparts forces to a patient's teeth. Example materials include one or more polymeric materials.

Although photobiomodulation (e.g., the application of light to tissue) has been suggested as one method of increasing the rate of tooth movement of teeth and/or provide forms of therapy to a patient's oral tissue, many orthodontic systems do not use photobiomodulation. Additionally, while it may be beneficial for orthodontic systems to use various factors for the use photobiomodulation on oral tissue (placement, timing (duration), method of delivery, etc.), existing systems have not been able to successfully do so. Further, little has been done to provide devices that can combine the application of specific dosing of energy (e.g., photobiomodulation energy) and controlled tooth movement in order to improve orthodontic outcomes.

SUMMARY OF THE DISCLOSURE

Described herein are methods and apparatuses (including dental appliances) that provide highly controlled and potentially more effective combinations of energy, including photobiomodulation energy, via an orthodontic appliance and/or series of appliances that are specifically adapted for the precise and combined application of energy and force to a patient's teeth. The methods and apparatuses herein may deliver light energy to oral tissue (teeth, gums, etc.) using light sources that can accelerate treatment, provide forms of heat therapy to portions of patients' oral tissue, and provide other benefits to patients.

In general, described herein are orthodontic aligners that may apply radiative energy (e.g., heat, light, electrical energy, etc.) to the dental arch in addition to mechanical force to the teeth in order to enhance tooth movement. In some variations the heat or light energy may be applied only to specific sub-regions of the dental arch and/or only a certain times during a treatment plan.

For example, described herein are methods and apparatuses that include an aligner (or other dental apparatus, such a palatal expander), that are configured to apply optical energy (e.g., light) using one or more light sources and may guide the light to one or more region of the dental arch using the aligner to focus, channel and/or filter the light. Any appropriate wavelength of light may be applied (e.g., visible light, infrared/near-IR light, etc.) including any appropriate range or sub-range of light frequencies.

For example, the methods and apparatuses describe herein may include an aligner body within which a light source attached, included or configured to be coupled (e.g., to a light-input), and the light may be distributed by the aligner body. For example, in some variations the aligner may include one or more optical fibers, light waveguides, light pipes, etc., for guiding the light to one or more regions of the appliance for delivery to the body. In some variations the light may be diffused through all or a portion of the aligner that has optical properties sufficient for distributing and delivering the light through the material in order to expose the nearby tissue (e.g., one or more of the teeth, gingiva, palate, etc. and/or specific regions thereof).

For example, in some variations the apparatus may be configured to channel the light from a light source (e.g., an LED within the apparatus) to one or more specific regions of the appliance. In one variation, the appliance (e.g., aligner) may include a sub-region of the teeth and/or the gingiva of the region of the patient's dental arch that the current or a subsequent appliance is configured to delivery mechanical force to move one or more teeth. For example, in some variations the appliance include a light source and an optical channel (e.g., light guide, waveguide, light-transmitting channel) between the light source and a portion of the appliance that is adapted to expose the portion of the dental arch to be modified by the current or a subsequent (immediately subsequent) appliance. For example, the optical channel may include a diffuser (e.g. diffusion film). In one example, the appliance includes an LED light source within the appliance and/or a light-input region that is connected via a light-transmitting optical channel through the appliance to a light output region that is limited to a portion of the appliance that applies a rotational and/or translational force to a specific sub-region of the dental arch (e.g., a molar, a bicuspid, etc.). In some variations this may be a single tooth and/or a group of adjacent teeth.

In general, the apparatus may be configured in conjunction with a pre-determined treatment plant. For example, a treatment plan may include a sequence of two or more dental appliances (e.g., aligners, expanders, etc.) configured to sequentially move, e.g., and align, a patient's teeth during the treatment. A series of aligners may be used to reconfigure the dental arch. The application of energy (e.g., light and/or heat and/or electrical energy) may be applied to aid in the movement of the targeted teeth. As mentioned, in some variations the teeth (or more typically tooth) being moved during a particular "stage" of the treatment plan corresponding to a particular appliance may include an energy output targeting the teeth/tooth being moved during that stage. Alternatively or additionally, a particular aligner may be configured to apply energy (e.g., light and/or heat and/or electrical energy) to the tooth or teeth being targeted in the next or subsequent stage of the treatment plan. For example, a series of aligners may sequentially move the teeth and each aligner may include energy outputs on the body of the aligner for delivering energy (e.g., light and/or heat and/or electrical energy) that specifically targets the tooth/teeth to which mechanical force is applied to move the tooth/teeth; alternatively or additionally, all or some of the aligners may include energy outputs on the body of the aligner that apply energy to the tooth/teeth to be moved by the next aligner in the sequence of aligners.

In variations in which optical energy is applied by the appliance, any of these variations may include one or more optical components within the body of the appliance that focuses, directs and/or filters the optical energy. For example, in some variations the appliance may include one or more lens, grating, filter, etc., such as a fiber bragg grating, etc. The optical component may be at or part of the energy (e.g., light) output. For example, the light output portion of the appliance may include a lens. In some variations the light output may include a diffuser or diffuser film; e.g., the output surface may be etched or otherwise adapted to direct light out of the appliance into the patient's tissue.

In some variations a light source such as an LED and/or a power source for the light source may be incorporated into the appliance. For example, the appliance may include a single LED that is held in a portion of the appliance that is relatively innocuous from the perspective of the patient, so as not to interfere with the patient's comfort, intercuspation and/or aesthetics. For example the light source may be held on the buccal side of the aligner, near the molar region (e.g., posterior); light emitted by the light source may be transferred through the appliance to a different region of the appliance specifically for output to a target region.

Any of these apparatus may include a controller including one or more processors, control circuitry and/or timers. The controller may regulate the power applied (e.g., the power applied to the light, and/or the power directly applied to the patient). Any of these controllers may also or alternatively be configured to deliver energy for a predetermined period during a treatment or multiple times during a treatment (e.g., in a dose pattern). For example, in some variation energy may be applied at a predetermined time or times during the day, for a specific period (e.g., for 30 seconds, 1 minute, 2 minutes, 5 minutes, 10 minutes, 15 minutes, 20 minutes, 30 minutes, 45 minutes, 1 hour, 1.5 hours, 2 hours, 3 hours, etc., or more). In some variations the controller may be configured to initiate an energy treatment based on an input, including a control input (e.g., from a wireless communications signal received by the controller, etc.). In some variations the energy treatment may be initiated in the appliance when the processor detects a preset condition. For example, in some variations the appliance may include a motion detector. Treatment may start/stop based on detected motion; for example, when the patient is relatively quiescent (e.g., no movement of the body/head and/or jaw), as may occur during rest, which may be detected by the motion sensor. This may be used as a safety control, as well. For example, the application of energy (e.g., light) may be limited to periods when the patient's mouth is closed. Instead or in addition to motion sensors, any other sensor (e.g., proximity sensor, where proximity is proximity to the adjacent jaw, etc.) may be used to turn the delivery of energy on/off. For example, a sensor and controller may be configured to determine when the patient's mouth is closed, and may apply the energy only when the patient's mouth is closed.

The controller may be integrated with or into the appliance, either in the same region as the energy source or at a different region. For example, the controller may be located on or in the buccal side of the appliance, or in any other region that may keep it from interfering with the patient's comfort, aesthetics and/or intercuspation.

Any of the apparatuses described herein may include one or more sensors that are configured to sense or estimate movement and/or resistance to movement of the patient's teeth and may adjust the application does of energy to the teeth accordingly. For example, in some variations the apparatus may include one or more force sensors configured to determine when the tooth is resisting movement from the force applied by the aligner on the teeth and may increase or decrease the applied energy (e.g., light and/or heat and/or electrical energy) accordingly.

The controller may generally be configured to set or modify the dose of energy applied. For example, the controller may be configured to limit the amount of energy applied to the tissue, which may prevent damage to the tissue. For example, a controller may include or may communicate with a dose monitoring subsystem that tracks the energy (e.g., light) delivered to the patient's dental arch and/or sub-regions of the dental arch. Any of the controllers described herein may include power regulating circuitry that regulated and/or limits the applied power to prevent damage to the tissue. The controller may include a memory to store and/or track power delivered to the patient. In general, the controller may be a microcontroller.

In any of these variations, the appliance may include a manual control input (e.g., button, switch, etc.) that may be used to turn on/off and/or adjust a delivered dose. For example, and embedded switch or button may be included; in some variations the control is a pressure sensitive switch or button that is activated by applied pressure and/or force (e.g., by pushing with the finger, etc.). The control may be coupled to the controller directly or indirectly and may be used to start/stop or override control of the controller to delivery treatment.

In some variations the apparatus is configured for passive transmission of power (e.g., light and/or heat and/or electrical energy) through the appliance to the dental arch and/or a subset of the dental arch. For example in some variations an energy input region is included (e.g. on the front buccal side) for attachment to an energy source; the energy is directed onto/into the energy input region and is transmitted through or into the apparatus for delivery to one or more regions of the dental arch. For example, a light source (including a phone or other hand-held light source) may be placed on or near the energy input and energy may enter the appliance through the energy input and be directed by the appliance (e.g., through an energy delivery channel within the appliance) to an energy output region of the appliance for delivery to all or a specific target sub-region of the dental arch. Thus, in any of these apparatuses a generic energy (e.g., light, heat, electrical power) source may be used in conjunction with the appliance to apply energy to the patient. For example, a system as described herein may include an appliance having a light input region and a separate or separable light source.

In any of the apparatuses described herein the aligner may be configured to communicate with one or more external devices. For example, in some of these variations the appliance may be configured to receive and/or transmit data between the appliance and an external processor. The external processor may be a smartphone or other portable computing device which may be a dedicated device or a general purpose device (e.g., smartphone) running an application (e.g. "app") or other software. The external processor may in turn connect to a remote device (e.g., remote server). The external processor may sent instructions or commands to the appliance and/or may store, analyze and/or transmit data from the appliance. The appliance may communicate directly (via a cable, wire, cord or other plug-in) or wirelessly (e.g., via a WiFi, Bluetooth, ZigBee, ultrasound or any other wireless technology). For example, in some variations the apparatus may communicate wirelessly using the energy applicator. Thus, in any of these devices the energy applicator (e.g., light or electrical energy applicator) may be configured to transit and/or receive information, including data, to an external processor. In some variations, the apparatus is configured to deliver infrared (IR) energy (including near-IR energy) to the patient's teeth. The same IR transducer may be used as a communications output; for example, the apparatus may modulate the applied energy (e.g., IR) to deliver information through the aligner material.

In some variations, the transmission of information by the applied energy source may also be used to wirelessly communicate with one or more components on the appliance, such as one or more actuators, including actuators for changing or adjusting the configuration of the appliance (e.g., increasing or decreasing the force applied to the teeth/tooth by the appliance). This control may therefore be performed without requiring additional connectivity. The actuator may instead be configured to receive the energy (e.g., lights, electrical energy, etc.) directly for control purposes.

Although the methods and apparatuses described herein may be configured for the application of energy, an in particular light energy, to modify the patient's dentition, in some variations these apparatuses may be configured to provide light for aesthetic purposes (e.g., as a decoration or ornamentation); this may be included in addition to or instead of the therapeutic purposes.

Some variations of the systems and methods described herein include embedding LEDs in an orthodontic aligner. Embodiments of the present disclosure also provide systems and methods of an orthodontic device for accelerating an orthodontic treatment, the device comprising a body comprising two or more tooth engagement regions configured to fit on to teeth, wherein the tooth engagement regions each comprise an occlusal side, a lingual side and a buccal side, further wherein the body is configured to apply a local force to a first region of a dental arch, and an emitter configured to locally radiate light energy to the first region of the dental arch. A "local force," as used herein, may include one or more repositioning forces that are applied to a specific area proximate to a region of a dental arch. The specific area may correspond to the immediate surroundings of the region of the dental arch. In some variations, the specific area may include an area of a specified distance (e.g., any value of 0.1 mm-5 mm) surrounding the region. "Locally radiating energy," "locally emitting energy," and/or "locally applying energy" as used herein, may include radiating, emitting and/or applying energy around a specific region of the dental arch and/or the resulting energy. In some implementations, locally radiating, emitting, and/or applying energy may include providing energy such that the energy has a first, more significant energy and/or intensity level in a specific area around the region of the dental arch and such that the light has a second, less significant energy and/or intensity level outside the specific area. The specific area may correspond to the immediate surroundings of the region of the dental arch. The specific area may include an area of a specified distance (e.g., any value of 0.1 mm-5 mm) surrounding the region. Additionally, in some implementations, the energy and/or intensity levels associated with a source of locally radiating/emitting/applying energy may fall to within a specified number of deviations (relative to their values at the source) outside the specific area. As examples, the energy and/or intensity levels associated with a source of locally radiating/emitting/applying energy may fall to within one, two, three, etc. standard deviations (relative to their values at the light source) outside the specific area.

Embodiments of the present disclosure also provide systems and methods of embedding heating elements in an orthodontic aligner. Embodiments of the present disclosure also provide systems and methods of an orthodontic device, the device comprising a body comprising two or more tooth engagement regions configured to fit on to teeth, wherein the tooth engagement regions each comprise an occlusal side, a lingual side and a buccal side, further wherein the body is configured to apply a local force to a first region of a dental arch, and one or more heating elements within the body configured to emit heat.

Embodiments of the present disclosure also provide a method of modifying a dentition using the orthodontic aligner or a palatal expander with a focal emitter. Embodiments of the present disclosure also provide a method of operating an orthodontic appliance using the orthodontic aligner or a palatal expander with heat.

For example, described herein are orthodontic devices for accelerating an orthodontic treatment, the device comprising: a body comprising two or more tooth engagement regions configured to fit on to teeth, wherein the tooth engagement regions each comprise an occlusal side, a lingual side and a buccal side, further wherein the body is configured to apply a local force to a first region of a dental arch to move one or more teeth of the dental arch; and an emitter configured to locally radiate energy to the first region of the dental arch.

The emitter may be configured to emit thermal energy (e.g., heat and/or cooling). The emitter may be configured to emit electrical and/or electromagnetic energy (e.g., may include one or more antennas configured to direct electrical, magnetic and/or electromagnetic energy (including, for example, pulsed electromagnetic energy, such as between 1 kHz and 100 kHz). The emitter may be configured to emit light energy.

The emitter may be configured to locally or focally deliver energy to the dental arch. For example, the emitter may be configured to emit prevent the emitted light from regions adjacent to the first region. The emitter may include a light source (e.g., one or more LEDs). The light source may include a near-infrared light source (e.g., emitting in the near-IR frequency range). The emitter may comprises a light channel within the body and an output window in the tooth engagement region and configured to be positioned adjacent to the first region when the device is worn on the dental arch. In some variations, the emitter includes a light input on an outer surface of the body configured to receive light from an external light source, wherein the light input is connected to the emitting through the body by a light guide. In some variations, the emitter is configured to emit the light energy along an edge region of the aligner. The emitter may be configured to emit light through one or more diffusion patterns etched on the aligner. The emitter may further include a filter for the light energy.

Any of these apparatuses may include a controller (e.g., control circuitry, including one or more processors, and/or timers) on the body configured to modulate the energy emitted by the emitter. For example, the apparatus may include a controller configured to modulate (e.g., turn on/off) the energy based on sensed data comprising detection of pressure or position of the teeth.

In any of these apparatuses and methods described herein, the body may be configured as an orthodontic aligner. In some variations, the body is configured as a palatal expander, further comprising a palatal region extending between the two or more tooth engagement regions, wherein the palatal region is configured to apply between 8 and 160 N of force between the pair of tooth engagement regions when the apparatus is inside a mouth.

An orthodontic aligner device for accelerating an orthodontic treatment may include: an aligner body comprising two or more tooth engagement regions configured to fit on to teeth, wherein the tooth engagement regions each comprise an occlusal side, a lingual side and a buccal side, further wherein the body is configured to apply a local force to a first region of a dental arch to move one or more teeth of the dental arch; and a light emitter configured to locally radiate light from a first region of the aligner body onto a local region of the dental arch, the light emitter comprising: a light source coupled to the aligner body at a second region of the aligner body, a light output on the aligner body configured to apply light on the local region of the dental arch, and a light channel extending from the light source to the light output through he aligner body. The emitter may be configured to prevent the light from being emitted from regions adjacent to the first region (e.g., may be configured to specifically apply energy, e.g. focally, to target teeth and/or gingiva associated with the target teeth). As mentioned, the light source may be a near-infrared light source.

The light channel may comprise an optical fiber within the aligner body. The emitter may be configured to emit light through one or more diffusion patterns etched on the aligner, through a lens and/or through a filter.

As mentioned, any of these apparatuses may include a controller on the body configured to turn the light on and off, to deliver a dose of light. The controller may be configured to cause the emitter to deliver light based on sensed data. The sensed data may comprises one or more of: movement, jaw position, tooth position, force or pressure on one or more teeth.

Also described herein are methods of orthodontically repositioning a patient's teeth. For example, a the method may include: positioning a first aligner (of a series of aligners to be worn in a predetermined sequence) on a patient's dental arch to apply a local force to a first region of the dental arch to move a first one or more teeth of the dental arch; locally applying light and/or heat and/or electrical/electromagnetic energy from the first aligner to the first one or more teeth of the dental arch and/or to the gingiva adjacent to the first one or more teeth; and then positioning each of a plurality of subsequent aligners (in the sequence) on the patient's dental arch to apply subsequent local forces to one or more additional regions of the dental arch and locally applying, from each subsequent aligner, light and/or heat and/or electrical/electromagnetic energy from each subsequent aligners to the one or more additional regions of the dental arch. The energy applied by each aligner in the sequence may be focally applied (e.g., may be primarily delivered, such as >70%, 75%, 80%, 85%, 90%, 95%, etc. delivered, to the target teeth/tooth and/or gingival region associated with the target tooth/teeth. Locally applying light and/or heat and/or electrical/electromagnetic energy may include applying light through an energy (e.g., light channel, thermal conductor, antenna/electrical conductor) within each aligner to the patient's teeth. Locally applying light and/or heat and/or electrical/electromagnetic energy may include applying energy from an external source. The locally applying light and/or heat and/or electrical/electromagnetic energy may include comprises applying light and/or heat and/or electrical/electromagnetic energy from a source integral to each aligner.

Locally applying light and/or heat and/or electrical/electromagnetic energy may involve applying light and/or heat for a predetermined dose while the patient is wearing each aligner. In some variations, locally applying light and/or heat and/or electrical/electromagnetic energy may involve applying light and/or heat and/or electrical/electromagnetic energy based on data from a sensor on each aligner. In some variations, locally applying the light and/or heat and/or electrical/electromagnetic energy may comprise applying light and/or heat when the patient's mouth is closed (e.g., but not when the mouth is opened).

Additional objects and advantages of the disclosed embodiments will be set forth in part in the following description, and in part will be apparent from the description, or may be learned by practice of the embodiments. The objects and advantages of the disclosed embodiments may be realized and attained by the elements and combinations set forth in the claims.

It is to be understood that both the foregoing general description and the following detailed description are example and explanatory only and are not restrictive of the disclosed embodiments, as claimed.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1F illustrate views of an example prior art apparatus for administering LED light to dental arches, through a patient's cheeks.

FIG. 2A illustrates an example of a first and second orthodontic device, consistent with embodiments of the present disclosure.

In FIG. 4A, the aligner is configured to emit energy from the bottom edge region of the aligner.

DETAILED DESCRIPTION

Figure 2B:
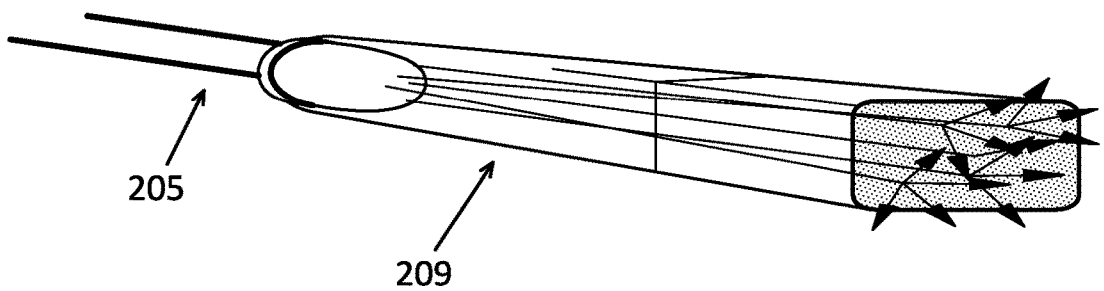
FIGS. 2B and 2C illustrate one example of a light-transmitting optical channel and light source that may be included with an appliance as described herein.

In general, described herein are methods and apparatuses (e.g., systems, devices, etc., including in particular orthodontic appliances, such as, but not limited to, aligners and palatal expanders) that can deliver energy, and particularly local radiant energy such as one or more of light, heat and/or electrical/electromagnetic energy to one or a subset of a patient's teeth and/or associated gingival region.

Reference will now be made in detail to example embodiments. Examples of which are illustrated in the accompanying drawings. The following description refers to the accompanying drawings in which the same numbers in different drawings represent the same or similar elements unless otherwise represented. The implementations set forth in the following description of example embodiments do not represent all implementations consistent with the invention. Instead, they are merely examples of systems and methods consistent with aspects related to the invention as recited in the appended claims.

As described herein, photobiomodulation may include low-level laser therapy. Photobiomodulation has been used to relieve short-term pain and to influencing metabolic rate and tissue metabolism, especially after surgery. Photobiomodulation is may be applied using other forms of energy, for example light from a light emitting diode (LED), heat from heating elements, and radio frequency (RF) energy from radio waves.

FIGS. 1A-1F illustrate various views of one example of a device 100 for administering LED light to dental arches, through the patient's cheeks. This delivery mechanism may be sub-optimal. This device 100 is divided into 4 sections 101, 102, 103, and 104. In operation, a patient wears the device on the face area that covers the dental arches. The 2 upper sections, viz. 101 and 102 are placed between the nose and the upper lip, while the 2 lower sections, viz. 103 and 104 are placed below the lower lip and encompassing the chin. The patient's face supports device 100 by a looped ridge 105 that loops the bridge of the patient's nose, clamp-like structures 106 generally placed on each of patient's cheek, and looped ridges 107 that loop over patient's ears. An array of LEDs 108 are each placed on the underside of sections 101-104 such that when the patient wears the device, the LEDs are in contact with the patient's skin area covering the dental arches and generally aimed at the four quadrants of the dental arches.

The device of FIG. 1 is bulky, cumbersome to wear, and may be difficult to properly adjust to project the LEDs onto the dental arches. Further the light from the LEDs must project through the patient's skin only onto the buccal side of the patient's dentition. In this configuration, light is not projected onto the occlusal or lingual side of the patient's dentition.

Described herein are orthodontic appliances that may address these shortcomings. In general, these appliances apply force to move (e.g., rotate, translate, etc.) one or more teeth in small increments. Specifically, described herein are methods and apparatuses for emitting energy, such as one or more of light, thermal (heat), and/or electrical/electromagnetic energy directly to the subject's teeth, gingiva associated with the subject's tooth/teeth, and/or both. The energy may be focally delivered to the same teeth and/or gingiva associated with the teeth that are to be moved by the orthodontic appliance. The energy may be applied before applying the mechanical force/pressure by the appliance, and/or during the application of force and/or pressure by the appliance. In some variations a controller (e.g., processor) in the appliance or in communication with the appliance may be used to control the dosing (on/off and in some variations modulation of the frequency, duty cycle, amplitude/intensity, etc.) applied. In some variations, one or more sensor may be used to determine when to apply the energy.

Figure 2C:
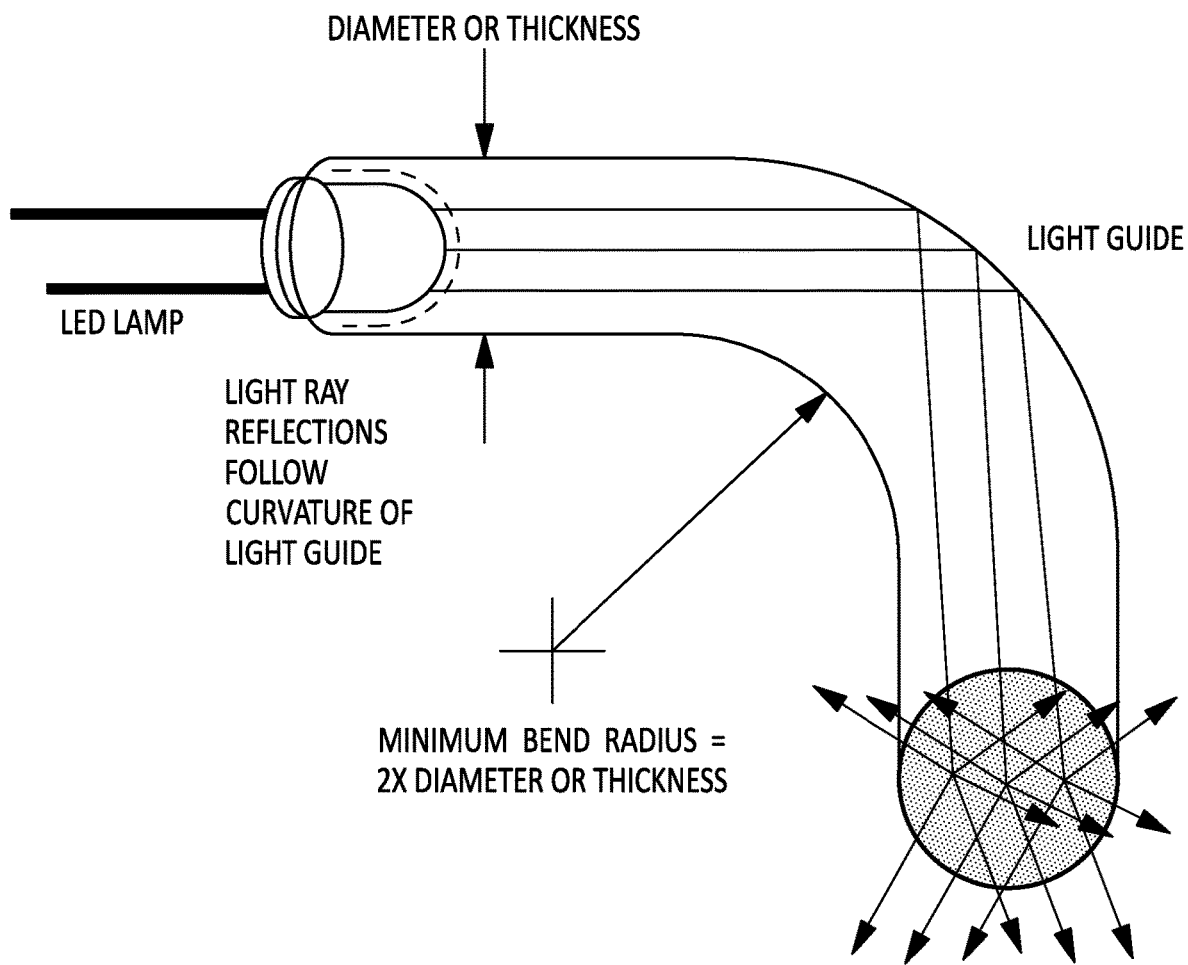

For example, any of the disclosed embodiments may provide systems and methods for accelerating orthodontic treatment by applying light energy. In any of these variations, the apparatus may include one or more embedding LEDs in the aligner(s) to improve photobiomodulation and for a more targeted therapy. Also provided are systems and methods for accelerating orthodontic treatment by adapting one or more regions of an aligner for targeting LED light, for example through light channel or guide 209 as shown in FIGS. 2A-2C, for example through a waveguide, to improve photobiomodulation and with a more targeted therapy. The light channel (e.g., waveguide, light pipe, etc.) may be in or of the body the orthodontic appliance. In some variations the light channel is a fiber optic. In some variations the light channel is embedded within the body of the appliance. In some variations the appliance is formed at least in part of a material that may be transparent to the applied energy which may pass it to the teeth and/or gingiva. In some variations the entire appliance may be configured to transmit energy (e.g., one or more of: light, heat, electrical/electromagnetic)

and radiate it to the dental arch on which it is worn, including the underlying gingiva.

FIG. 2A illustrates two embodiments of a light guide of an orthodontic device, consistent with embodiments of the present disclosure. The orthodontic device comprises an aligner 200 with a light source 205 external to aligner 200. In another example, an aligner 210 may include an embedded energy source 215 (e.g., light source) forming part of the emitter. Aligners 200 and 210 may be made from silicone or other appropriate materials and may be clear in color. The aligners 200 and 210 may include one or more properties of the appliances shown in FIGS. 8A and 8B.

In some variations the aligner(s) 200 and/or 210 may be at least partially opaque and may be colored (e.g., white or other color similar to the patient's native teeth). According to some embodiments, the emitter is configured to impart light from an LED source or a generic light source such as a flash on a smart phone, or alternatively direct light using fiber optics. According to some embodiments, the emitter is configured to impart heat from heating elements, for example heat activated actuators.

According to some embodiments, aligner 200 has one or more regions etched, for example etched region 206, etched region 207, and etched region 208 may reside on the respective occlusal, buccal, and lingual side(s). According to some embodiments, aligner 210 is embedded with emitter 215 along one or more of an edge region of the aligner's occlusal, buccal, and/or lingual edge. The embedded emitter or the etched regions may be prescribed into zones corresponding to the various regions of the dental arches as dictated by the patient's treatment plan. The emitter, for example emitter 205, may illuminate or heat specific areas of aligner 200, for example etched regions 206, 207, and 208. Or, the emitter, for example emitter 215, may illuminate or heat a continuance portion of the aligner, for example as shown in aligner 210. In both configurations of the orthodontic device, viz. an aligner with an emitter external to the aligner, or an aligner embedded with an emitter, the aligner provides a targeted and customizable illumination or heat that is patient specific.

In operation, the energy (e.g., one or more of: illumination, heat, electrical/electromagnetic) may be coordinated with a virtual treatment plan, turned on at certain times of the day, prescribed as a response to teeth movement, or prescribed near teeth that are not tracking as required. For example, teeth positions may be determined (e.g., by scanning). Next, the treatment plan may be overlaid by the scan, before the emitter is turned on to direct the illumination or heat to teeth with a large discrepancy. In accordance with another example operation procedure, the aligner may activate the emitter based on data sensed from pressure or position of the teeth, or from lagging teeth. The data sensed from pressure or teeth position, or from lagging teeth may be detected, for example using pressure sensors, accelerometers, fiber optics Bragg grating, or a pressure sensitive switch.

Activation of the emitter may be accomplished wired or wirelessly using a "passive" regulating circuit. Further, the intensity and duration of the illumination or heat may be static or dynamically predefined based on the treatment plan or defined manually. According to some embodiments, the intensity and duration of the applied energy (e.g., illumination, heat, electrical/electromagnetic energy) may be controlled using limiting circuits, microcontrollers, or response-based, i.e., illumination or heat is turned off when the result of the treatment plan is accomplished from the inference of the teeth.

According to some embodiments, the aligner, for example aligners 200 and 210, may be used as a near infrared filter, for example as a low pass filter for a flash on a smart phone, as a diffusion film, or as a redirector or modifier of the illumination.

According to some embodiments, the LEDs may be used for applications other than photobiomodulation. For example, the LEDs may be used to transfer data using infrared communication. One example method is using the aligner material similar to a fiber optic cable to transfer data. In another example, the LEDs may be paired with a photodiode, light sensor, or camera for detecting proximity of spacing between teeth, surface detection, or to map radiation properties such as absorptivity and transmissivity to physiological properties.

Figure 3A:
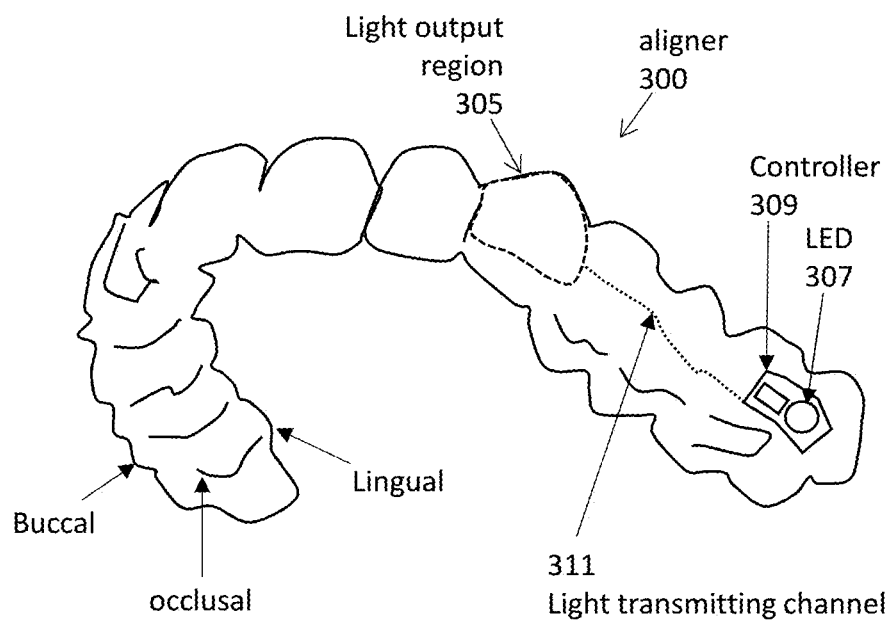
FIGS. 3A and 3B show bottom perspective and top perspective views, respectively, of an example of an appliance, configured as an aligner, adapted to deliver energy (e.g., light) to a patient as described herein, including an integrated energy source (e.g., light source), a light-transmitting channel, a controller, and an energy (e.g., light) output region.
Figure 3B:
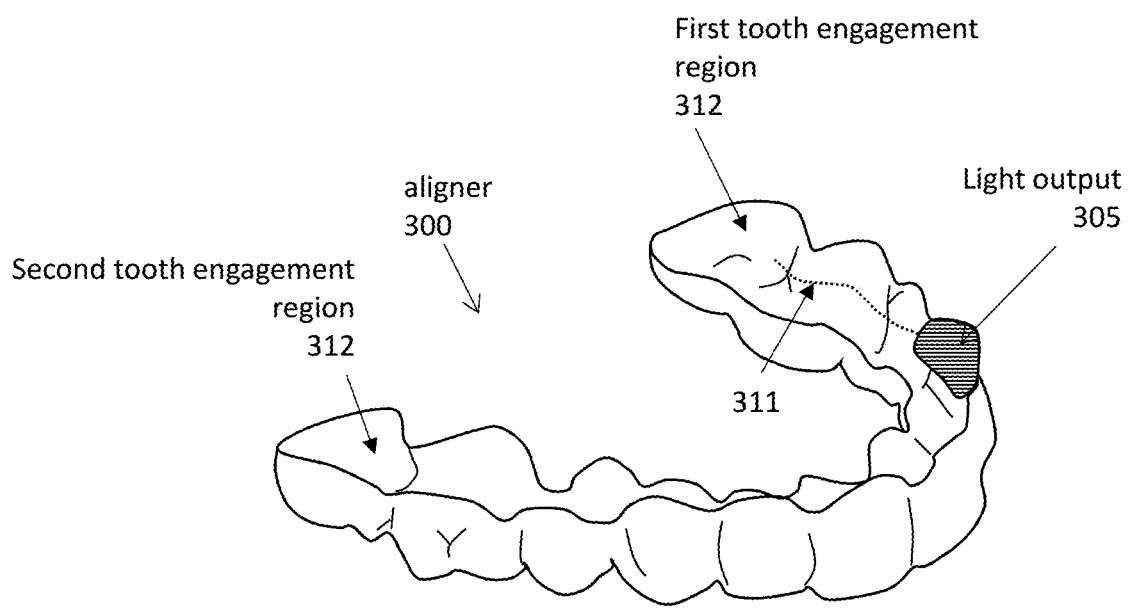

For example, FIGS. 3A-3B illustrate an example of an dental appliance 300 that is configured to apply light energy to a patient's teeth as part of an orthodontic treatment. The appliance (e.g., dental appliance 300) in this example, includes the light output region 305 to output light onto one or more tooth/teeth to be moved and/or the tissue (e.g., gingiva) around the tooth to be moved. It is noted the dental appliance 300 may include one or more properties of the appliances shown in FIGS. 8A and 8B.

The dental appliance 300 also includes a controller 309 and light source 307 that provides light (as controlled by the controller) to the light output through a light transmitting channel 311. In FIG. 3A, which shows a perspective view of the outside surface of the dental appliance 300, the light output region 305 is shown by the dashed lines, as in some variations the light may be directed to an edge region of the dental appliance 300 that faces the teeth/gingiva (e.g., the bottom edge region of the dental appliance 300 and/or the side within the tooth engagement region(s) 312. The light output region may be a window or transparent/semi-transparent region on or in the dental appliance 300. In some variations the material forming a region of the dental appliance 300 (e.g., the dashed region) may be configured as a diffuser region that receives the light from the light transmitting channel 311 for delivery onto the teeth. FIG. 3B shows the inner (tooth engagement region(s) of the dental appliance 300 300, showing the light output region 305. The light output region may be made of a material that is transparent (e.g., clear) or non-transparent but allows at least some of the light in a desired wavelength range (e.g., >40%, >50%, >55%, >60%, >70%, >80%, >90%, etc.) to be transmitted through the material. Thus an optical connection may be made between the light transmitting channel and the light output region. In some variations the light output region may be a light-transmitting material on at least one surface or side of the dental appliance 300 (e.g., the tooth engagement region side), which may be bounded by non-transmitting boundaries, including a back region (shown by the dashed lines in FIG. 3A) and/or the side regions adjacent to the light output. For example, these boundaries may be formed of a non-transmitting or lower-transmitting material, and/or may be coated or bounded by a reflective and/or non-transmitting or lower-transmitting material (e.g., a material allowing <50%, <40%, less than 30%, less than 20%, less than 10%, etc. of light in the emitting light range to pass). In some variation the boundary (and particularly the back region) may be reflective for the emitting light range. The emitting light range may also be referred to as the therapeutic light range.

The light transmitting channel in FIGS. 3A and 3B may be formed of a fiber optic and/or a channel of relatively highly transmissive material (light transmissive/transmitting material, e.g., for the therapeutic light range) which may be bounded by a less transmissive material. The light transmitting channel 311 may be enclosed and/or formed within the body of the dental appliance 300, as shown by the dashed lines in FIGS. 3A-3B. Alternatively or additionally, the light transmitting channel may be on the outer and/or inner surfaces. In some variations, this may allow a lower, potentially more comfortable, form factor.

In FIGS. 3A and 3B, the controller 309 is shown on an outer (buccal) side of the dental appliance 300 near the distal (molar) ends, and may be within the body of the dental appliance 300 and/or extend slightly from the body of the dental appliance 300. In some variations the controller may be housed in a housing or embedded directly into the dental appliance 300. For example the controller may include a control circuitry (e.g., chip) that may have a power regulator circuitry and/or a battery. The controller may include a timer, and in some variations a memory and/or communications circuitry. The controller may be connected to one or more inputs (not shown) such as a button or pressure sensor. The controller may also receive input from one or more sensors that may provide input data to determine when to activate/deactivate the light source 307 delivering light to the light transmission channel and therefore to the light output 305. In some variations the controller may include a clock and/or timer circuitry to determine when and how long to apply a dose. The controller may be pre-programmed, and/or may communicate with one or more external processors (e.g., remote processor) that is configured to regulate the on/off and/or intensity (pulsing rate, amplitude/intensity of light, etc.).

In general, the appliance (e.g., dental appliance 300) shown in FIGS. 3A-3B may also be configured as part of a treatment plan that includes applying mechanical force to move (e.g., translate, rotate, etc.) one or more teeth. Thus, the tooth/teeth being moved by an dental appliance 300 (at a corresponding stage of the treatment plan) may be the same tooth/teeth (or corresponding soft tissue around the target tooth/teeth) to which the light is being selectively and/or specifically delivered. Alternatively or additionally, an dental appliance 300 in a treatment plan may be configured to apply light to a region that is to be moved next in the treatment plan. For example a first dental appliance 300 may be configured to apply light energy to a tooth being moved and, partway through the treatment, or towards the end of the treatment period wearing that dental appliance 300, may illuminate the next tooth/teeth that will be moved by the next dental appliance 300 in the treatment plan, to prepare these next tooth/teeth to be moved immediately upon waring the next dental appliance 300. For example, if an dental appliance 300 of a treatment plan is to be worn for 14 days before the next dental appliance 300 in the treatment plan is to be worn, at day 11 (e.g., day 10, day 11, day 12, day 13, day 14), the controller may be configured to apply light energy to the next tooth/teeth to be moved; light may be continued to be applied to the current tooth/teeth to which force is being applied by the current dental appliance 300 in the treatment plan, or it may be discontinued.

Figure 3C:
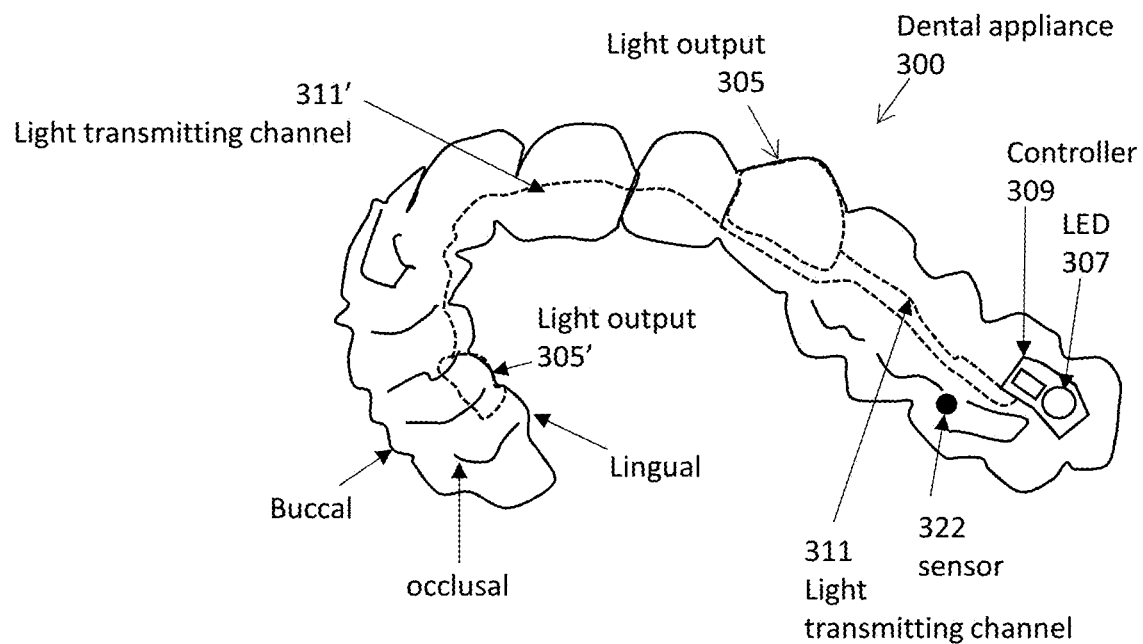
FIGS. 3C and 3D show an example of a dental appliance configured to emit light onto a wearer's teeth.
Figure 3D:
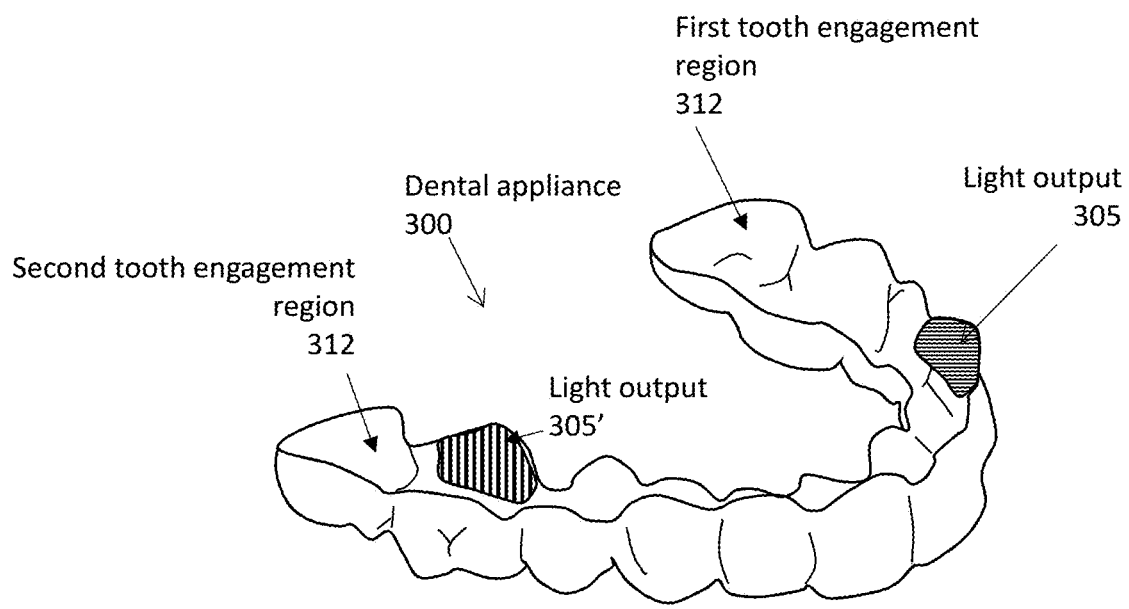

FIGS. 3C and 3D show an example of an dental appliance 300 configured to emit light onto two discrete tooth (or sets of teeth to be moved). As in FIGS. 3A-3B, the dental appliance 300 includes a first light output region 305 that is coupled via a light transmitting channel 311 to a light source (e.g., LED 307) controlled by a controller 309, which may include a processor and/or control circuitry and a power source (e.g., battery, not shown). In FIG. 3C, the dental appliance 300 also includes a second light output region 305' that is connected via a second light transmitting channel 311'. The first and second light transmitting channels 311 may be connected, or may be separate (as shown in FIG. 3C). FIG. 3D shows a view of the inner, e.g., tooth engagement, side of the dental appliance 300 of FIG. 3C. In FIG. 3D, the first light output region 305 and the second light output region 305' are shown. As mentioned, the light output regions may be bounded by a non-transmitting (in some variations, reflecting) region that prevents or limits substantial illumination of non-target regions, e.g., adjacent to the target tooth/teeth. The two regions may be concurrently illuminated, or may be separately controlled. For example, the controller 309 may control a switch that permits or prevents light from entering the first and/or second light transmitting channel 311, 311'. Alternatively or additionally separate light energy sources (e.g., LEDs) may be used for illuminating different regions. In the examples shown in FIGS. 3B and 3D the tooth engagement portion of the dental appliance 300, which mates with the patient's teeth, may be divided up into two or more tooth engagement regions; these tooth engagement regions may be separate (e.g., where a tooth is missing/extracted) or continuous with each other, as shown in FIGS. 3B and 3D.

In any of the variations described herein, different light sources (e.g., lights having different ranges of wavelength, e.g., optical to infrared) may be used. In some variations, a first range of wavelengths may be applied during first treatment dose (period) and a second overlapping or non-overlapping range of wavelengths may be applied during a second time period.

In some variations, the apparatus includes a light output region that extends over much or all of the dental appliance 300, rather than being limited to just the target teeth. However, the applied energy (e.g., light energy) may be applied just from an edge region of the dental appliance 300 (e.g., the edge region closest to the gingiva. In any of the dental appliance 300s described herein, the light is applied just from the inner (e.g., tooth-contacting side, e.g., the tooth engagement region) side of the dental appliance 300 and/or from the edge. In some variations, light may be emitted from light outputs spanning the entire dental appliance 300.

Figure 4A:
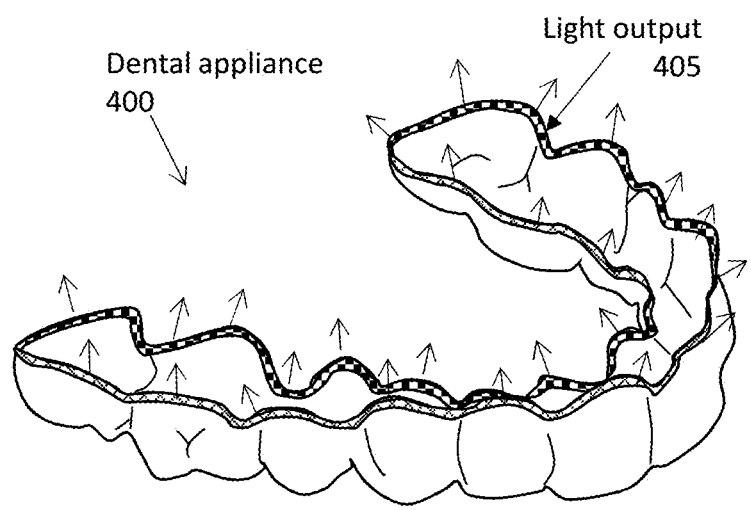
FIG. 4A shows another example of an aligner configured to emit energy (e.g., light energy, electrical/electromagnetic energy, etc.).

FIG. 4A shows an example of a dental appliance 400 configured so that energy (e.g., light) is emitted from an edge region of the apparatus. It is noted the dental appliance 400 may include one or more elements of the appliances shown in FIGS. 8A and 8B. The light output region 405 may extend along all or most of an inner and/or outer edge region. In FIG. 4A the light output region includes the edge and may extend slightly up the edge region. The inside edge region (e.g., within the tooth engagement region(s)), the outside edge (e.g., on the buccal or lingual sides), and the end/edge region of the dental appliance 400 between the lingual and buccal sides may be configured to radiate energy, as shown by the arrows in FIG. 4A. Alternatively, just the inside, e.g., tooth engagement side edge, and the end/edge itself may be configured to radiate energy.

Figure 4B:
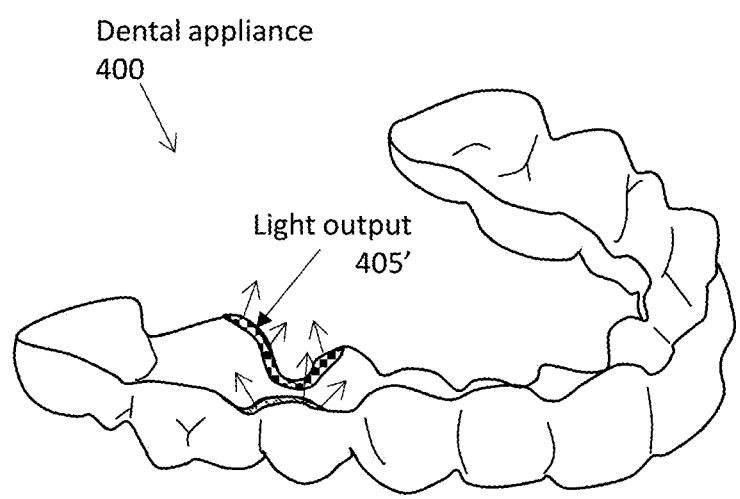
FIG. 4B is an example of an aligner configured to emit energy from a portion of the bottom edge region of the aligner, on either side of a target tooth or teeth.

In some variations, as shown in FIG. 4B, only the edge region 405' may radiate energy, and only a subset of the edge region (e.g., at or near a target tooth or set of teeth to which force is or will soon be applied). Multiple different regions may be separately controlled, as discussed above in reference to FIGS. 3C and 3D. In FIG. 4B, both sides of the target teeth (e.g., the lingual and buccal sides, may be illuminated, as shown in FIG. 4B. Alternatively only the buccal or only the lingual sides may be illuminated. Any of the energy, including light, output regions described herein may be at or substantially limited to the edge region of the appliance.

Figure 5:
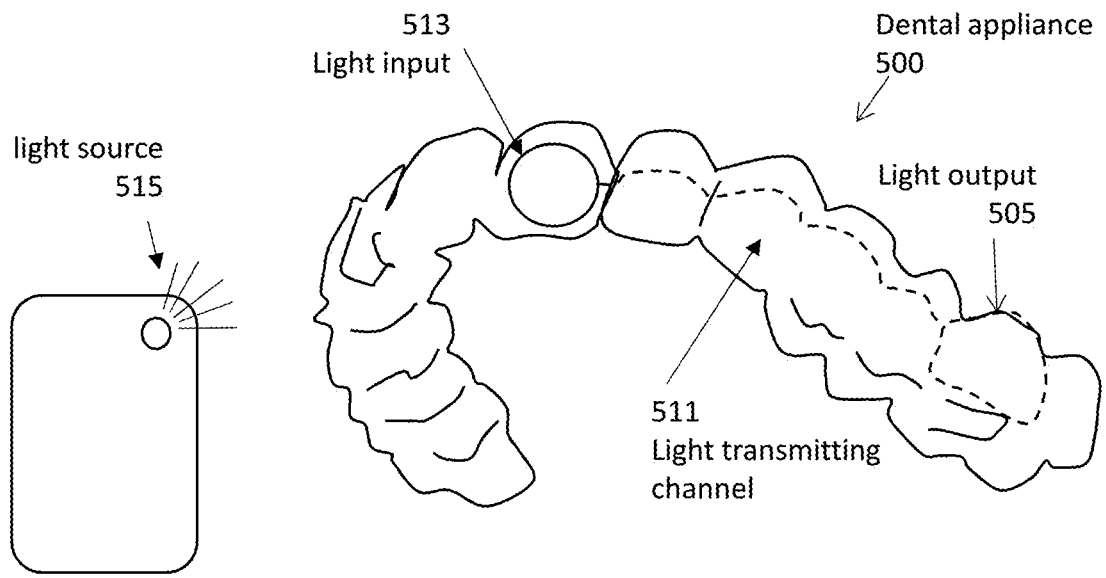
FIG. 5 is an example of an appliance, configured as an aligner, adapted to deliver energy (e.g., light energy) to a patient as described herein, having an energy input region, a light-transmitting channel, and a light output region.

FIG. 5 shows an example of a dental appliance 500 that does not include an energy source (e.g. light source) but instead includes an optical input region 513 into which light energy is applied by an external device (e.g., light source 515); the applied light is transferred to the target light output region 505 by a light transmitting channel 511, similar to that described above. In FIG. 5, the light input is may a window or other light-transmitting material, similar to that shown and described above for the light output regions, including the light output 505 in FIG. 5. Thus, the appliance may transfer light from the light source to the targeted light output region. Any appropriate light source 515 may be used. For example in some variations the light output may be the illumination source (flash, LED light) on a smartphone. For example, a user application software ("app") running on the patient/user's smartphone may be used to apply the energy to the dental appliance 500, instructing the patient when and for how long to hold the flash up to the teeth for a treatment dose. The app may also control the light source.

The light-emitting appliances described herein may also be used to emit light to communicate to the user. For example, in some variations visible light may be emitted by the device (e.g. as a color, such as red, blue, etc.) in a manner that is distinct from the therapeutic light delivered as described above, in order to signal to the user to remove or replace (or otherwise service) the appliance. For example, when it is time to replace the appliance, and/or move on to the next stage of treatment, the appliance may flash a light and/or illuminate (e.g. by emitting a distinct color) to let the user know it is time for the next treatment step. The controller may determine this timing based on a clock or other time, or in some variations based on detected tooth movement, forces and/or position.

Alternatively or additionally, in some variations the dental appliance 500 may be configured to focally apply heat energy (e.g., thermal energy) from the appliance. Thermal energy (e.g., warming) may be between 36 and 50 degrees C. (e.g., between 37-45 degrees C., etc.). It is noted the dental appliance 500 may include one or more elements of the appliances shown in FIGS. 8A and 8B.

Figure 6:
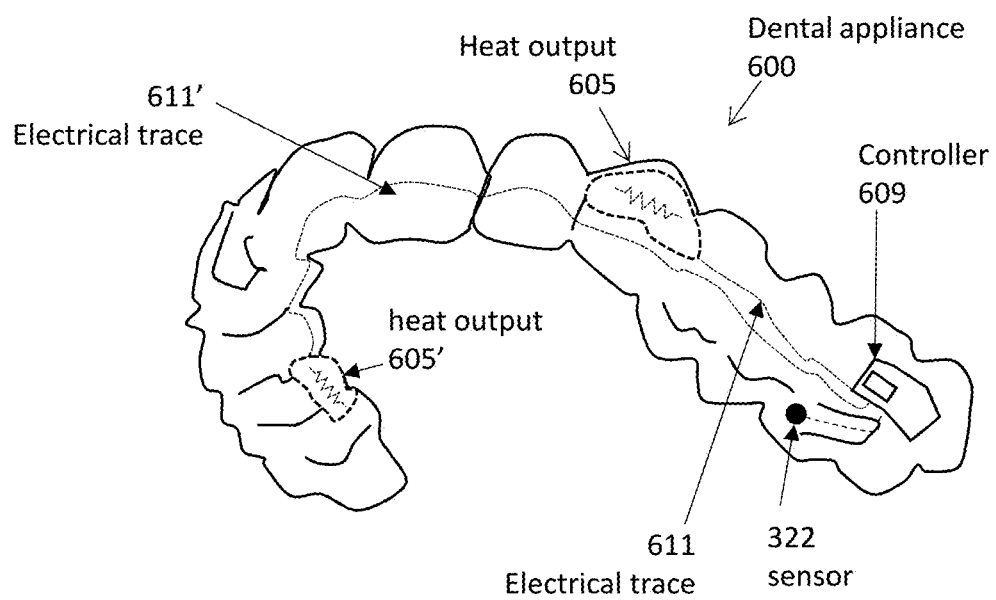
FIG. 6 is an example of an appliance configured as an aligner adapted to deliver thermal energy to a patient as described herein.

FIG. 6 illustrates an example of a dental appliance 600 configured to apply thermal energy (e.g., heat) to a region of a patient's mouth to help accelerate or otherwise improve an orthodontic treatment. In FIG. 6, the appliance includes a controller 609 that may include a power source (e.g., battery, etc.) that is electrically connected, e.g., via one or more conductive traces 611, 611' to one or more heater output regions 605, 605'. In FIG. 6, the heat output may include a resistive heating element that may be controlled by the controller to generate a predetermined heating profile; the heat output may include a thermistor for feedback control of the applied temperature. In some variations the material forming the heat output may be selected to have a relatively high thermal conductance, while adjacent/surrounding region(s) may be less thermally conductive, in order to help localize the applied temperature.

Thus, any of these apparatuses may be used to perform thermotherapy. For example, any of these apparatuses may be used to help provide rehabilitation after dental procedures or surgery. Any of these apparatuses may be used for pain management during orthodontic movement; this may include or be separately used for relief of inflammation, vasodilation, metabolic rate increase, etc., For example, thermal-energy applying apparatuses may be used to locally increase tissue metabolism (e.g., vasodilation, increased blood flow, occurs under increased temperature), and metabolic rate/tissue extensibility. This may lead to increased oxygen update and/or increase rate of tissue healing, as well increased activity of destructive enzymes and catabolic rate.

Any appropriate thermal emitter may be used. For example, the thermal emitter (heat emitter) may be a heating element, such as a resistive heating element. In some variations, a current source may be used. The current source may be induced externally. Alternatively or additionally, one or more antennas (e.g. "heater antenna") may be used. An antenna may be energized by external RF and may convert the RF energy to heat. Alternatively or additionally, one or more optical heating elements (e.g., hLight/infrared radiation sources) may be used. The duration and depth of heating may be varied. For example in some variations, superficial tissue or deep tissue heating may be applied, which may depend on the method (including the applied energy and/or the duration energy is applied) may be used to provide the heat. For example, in some variations the heating element is an ultrasound transducer. Ultrasound may allow for deeper tissue heating. Thus, in FIG. 6, for example, the heat output region(s) may include one or more ultrasound applicators that are configured to apply heat. In some variations, the heat source may be a chemical heat source.

As mentioned above, in any of these variations, the heating may be applied in a focal or targeted manner, which may be coordinated with one or more treatment plans, examples of which are discussed herein The treatment plan is typically patient-specific, and therefore the timing and/or location of the applied energy (e.g., heat) may be patient specific. As mentioned, one or more temperature sensors (e.g., thermistor) may be included, and the heating may be closed-loop.

In some variations, energy, e.g., heat, is applied in response to tooth movement or amount of force applied to teeth (and/or in response to a lack of tooth movement) in order to expedite or improve outcomes for an orthodontic treatment.

In any of the variations described herein, energy (e.g., light, heat, electrical, etc.) may be applied in response to patient activity, or only when the patient is resting (e.g. not talking, eating, etc.). For example, any of these apparatuses may include one or more sensors for detecting when the patient's jaw(s) is/are open or closed. For example, a pressure sensor (see, e.g., FIG. 3A, sensor 322) on an occlusal surface may determine when the jaws are closed for a substantial amount of time); other sensors may include proximity sensors and/or movement sensors. Thus energy (e.g., light, heat, etc.) may be applied only when the mouth is shot. Opening the mouth may automatically shut off the application of energy. For example, energy may be applied in response skeletal or jaw movement. A movement sensor may be placed anywhere on the appliance, including incorporated into the controller.

In general, the methods and apparatuses (and particularly the controller, or an app in communication with the controller) described herein may be used to control the timing of energy delivered by the apparatus. For example, energy may be applied 1×, 2×, 3×, 4×, 5×, 6×, or more times per day (e.g., 1-5× day, 1-4× per day, etc.), which may depend on the day of the week and/or the time since the applicator was first attached to the patient's teeth.

Any of these methods an apparatuses may also regulate the duration of applied energy (e.g., 30 seconds, 1 minute, 5 minutes, 10 minutes, 15 minutes, 20 minutes, 30 minutes, 40 minutes, 45 minutes, 50 minutes, 60 minutes, 1.2 hours, 1.5 hours, 2 hours, 3 hours, etc.). The energy may be applied at different times of the day (e.g., nighttime, daytime, morning, evening, etc.).

Any of the methods described herein may include coordinating the application of energy by the apparatus with one or more drugs (e.g., with drug therapy).

In variations in which heat is being applied in conjunction with mechanical force (e.g., to move one or more teeth) the application of heat and/or force may be coordinated. For example, a heat-activated actuator may be used to apply force to move (e.g., translate and/or rotate) a tooth. For example, heat-shaped memory (shape memory alloys or SMAs) may be used; the same heat applied to deliver the energy dose may be used to control the actuator to apply force to the tooth/teeth. In some variations more than one type of radiated energy (e.g., light, heat, and/or energy/electromagnetic energy) may be used in the same apparatus to treat the patient (e.g., concurrently, sequentially or at least partially overlapping). The controller may control the application of multiple energies to the patient.

In general, any of the apparatuses, including dental appliances and/or aligners, described herein may include one or more attachment coupling regions on the aligner configured to couple with one or more attachments bonded to the patient's teeth to help the aligner move the patient's teeth. The attachment may be configured to aid in application of energy (e.g., light, heat, etc.) to the teeth. In some variations the appliance may apply energy (e.g., light, heat, electrical/electromagnetic fields). For example, the applicator may be configured to transfer light from the appliance to the patient's tissue.

In some variation the application of energy (e.g., heat energy) may also or alternatively be used to help remove one or more attachments from the aligner. For example the stiffness of the appliance may be decreased by the application of heat; thus the local application of heat may be used to remove an attachment by making the aligner (or a portion of the aligner securing the attachment (or an adjacent region) more compliant, and therefore easier to remove.

Figure 7A:
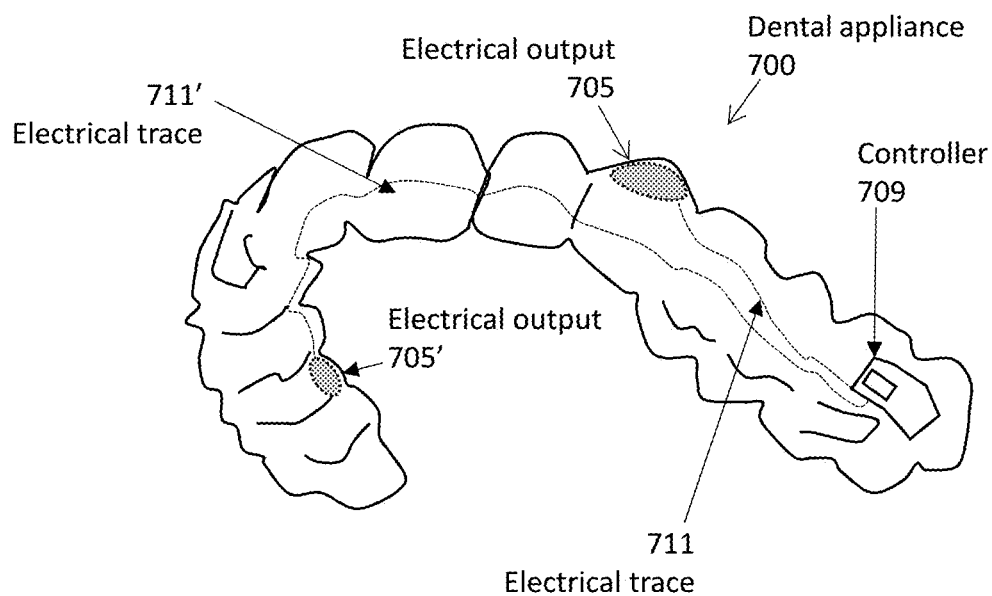
FIG. 7A is an example of an appliance configured as an aligner adapted to deliver electrical energy to a patient as described herein.
Figure 7B:
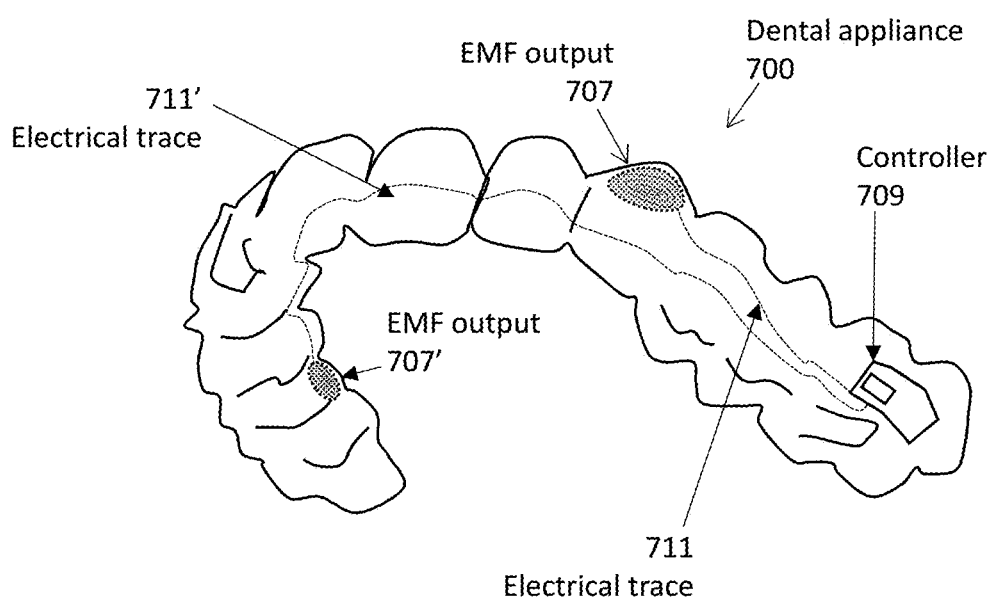
FIG. 7B is an example of an appliance configured as an aligner adapted to deliver electromagnetic energy to a patient as described herein.

FIGS. 7A and 7B illustrate examples of a dental appliance 700 configured to deliver electrical and/or electromagnetic energy (including but not limited to pulsed electrical magnetic energy) as described herein. In FIG. 7A the dental appliance 700 includes a shell body having one or more tooth engagement regions and is configured to apply force to move one or more teeth. The dental appliance 700 also includes an energy output 705 configured as an electrode (or pair of electrodes, e.g. anode and cathode, or live and ground, etc.) for delivery of electrical energy to the tissue associated with the one or more teeth to be moved. In FIG. 7, a first electrical output 705 and a second electrical output 705' are shown and are connected, via insulated electrical traces 711, 711' to a controller, which may include a power source (e.g., battery) and control circuitry, as described above. FIG. 7B shows a similar embodiment, in which the dental appliance 700 includes a pair of energy outputs 707, 707' configured as antennas that may emit electromagnetic energy (e.g., pulsed electromagnetic energy, PEMF). For example, the energy output may be a coil antenna.

As discussed above, a treatment plan may include the application of energy during one or more of the treatment steps. Thus, a treatment plan may be implemented by a plurality of the dental appliance 700 that are configured and/or adapted to emit energy to enhance the orthodontic treatment as described above.

Figure 8A:
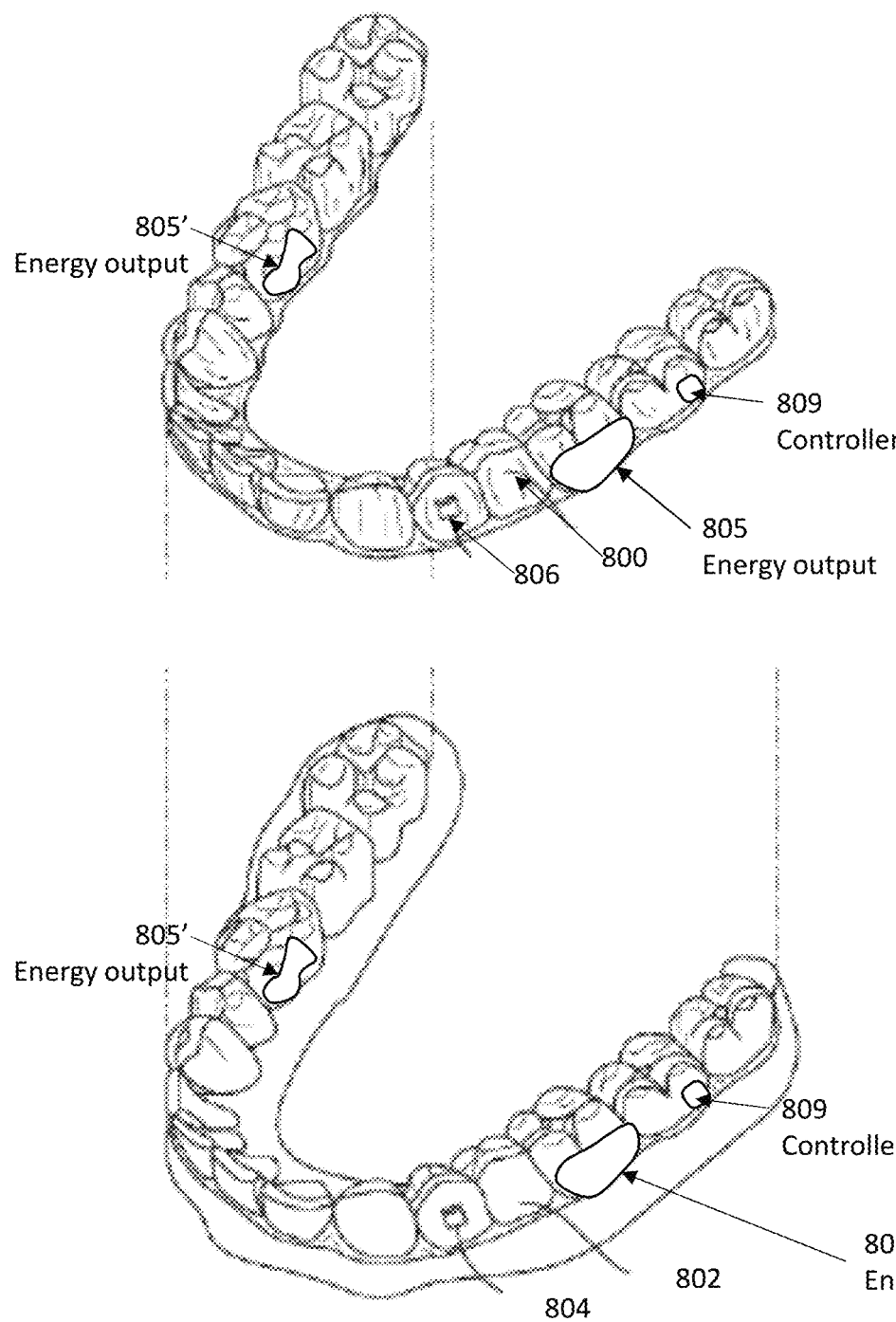
FIG. 8A illustrates a tooth repositioning appliance, in accordance with embodiments.

FIG. 8A illustrates an exemplary dental appliance 800 that can be worn by a patient in order to achieve an incremental repositioning of individual teeth 802 in the jaw. As shown in FIG. 8A, each of the dental appliance(s) 800 may include one or more energy outputs 805, 805', etc. and/or a controller 809 to drive and regulate the application of energy.

The dental appliance 800 can include a shell (e.g., a continuous polymeric shell or a segmented shell) having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. A "polymeric material," as used herein, may include any material formed from a polymer. A "polymer," as used herein, may refer to a molecule composed of repeating structural units connected by covalent chemical bonds often characterized by a substantial number of repeating units (e.g., equal to or greater than 3 repeating units, optionally, in some embodiments equal to or greater than 10 repeating units, in some embodiments greater or equal to 30 repeating units) and a high molecular weight (e.g. greater than or equal to 10,000 Da, in some embodiments greater than or equal to 50,000 Da or greater than or equal to 100,000 Da). Polymers are commonly the polymerization product of one or more monomer precursors. The term polymer includes homopolymers, or polymers consisting essentially of a single repeating monomer subunit. The term polymer also includes copolymers which are formed when two or more different types of monomers are linked in the same polymer. Useful polymers include organic polymers or inorganic polymers that may be in amorphous, semi-amorphous, crystalline or semi-crystalline states. Polymers may include polyolefins, polyesters, polyacrylates, polymethacrylates, polystyrenes, Polypropylenes, polyethylenes, Polyethylene terephthalates, poly lactic acid, polyurethanes, epoxide polymers, polyethers, poly (vinyl chlorides), polysiloxanes, polycarbonates, polyamides, poly acrylonitriles, polybutadienes, poly(cycloolefins), and copolymers. The systems and/or methods provided herein are compatible with a range of plastics and/or polymers. Accordingly, this list is not all inclusive, but rather is exemplary. The plastics can be thermosets or thermoplastics. The plastic may be a thermoplastic.

Examples of materials applicable to the embodiments disclosed herein include, but are not limited to, those materials described in the following Provisional patent applications filed by Align Technology: "MULTI-MATERIAL ALIGNERS," US Prov. App. Ser. No. 62/189,259, filed Jul. 7, 2015; "DIRECT FABRICATION OF ALIGNERS WITH INTERPROXIMAL FORCE COUPLING", US Prov. App. Ser. No. 62/189,263, filed Jul. 7, 2015; "DIRECT FABRICATION OF ORTHODONTIC APPLIANCES WITH VARIABLE PROPERTIES," US Prov. App. Ser. No. 62/189 291, filed Jul. 7, 2015; "DIRECT FABRICATION OF ALIGNERS FOR ARCH EXPANSION", US Prov. App. Ser. No. 62/189,271, filed Jul. 7, 2015; "DIRECT FABRICATION OF ATTACHMENT TEMPLATES WITH ADHESIVE," US Prov. App. Ser. No. 62/189,282, filed Jul. 7, 2015; "DIRECT FABRICATION CROSS-LINKING FOR PALATE EXPANSION AND OTHER APPLICATIONS", US Prov. App. Ser. No. 62/189,301, filed Jul. 7, 2015; "SYSTEMS, APPARATUSES AND METHODS FOR DENTAL APPLIANCES WITH INTEGRALLY FORMED FEATURES", US Prov. App. Ser. No. 62/189,312, filed Jul. 7, 2015; "DIRECT FABRICATION OF POWER ARMS", US Prov. App. Ser. No. 62/189,317, filed Jul. 7, 2015; "SYSTEMS, APPARATUSES AND METHODS FOR DRUG DELIVERY FROM DENTAL APPLIANCES WITH INTEGRALLY FORMED RESERVOIRS", US Prov. App. Ser. No. 62/189,303, filed Jul. 7, 2015; "DENTAL APPLIANCE HAVING ORNAMENTAL DESIGN", US Prov. App. Ser. No. 62/189,318, filed Jul. 7, 2015; "DENTAL MATERIALS USING THERMOSET POLYMERS," US Prov. App. Ser. No. 62/189,380, filed Jul. 7, 2015; "CURABLE COMPOSITION FOR USE IN A HIGH TEMPERATURE LITHOGRAPHY-BASED PHOTOPOLYMERIZATION PROCESS AND METHOD OF PRODUCING CROSSLINKED POLYMERS THEREFROM," US Prov. App. Ser. No. 62/667,354, filed May 4, 2018; "POLYMERIZABLE MONOMERS AND METHOD OF POLYMERIZING THE SAME," US Prov. App. Ser. No. 62/667,364, filed May 4, 2018; and any conversion applications thereof (including publications and issued patents), including any divisional, continuation, or continuation-in-part thereof.

Although polymeric aligners are discussed herein, the techniques disclosed may also be applied to aligners having different materials. Some embodiments are discussed herein with reference to orthodontic aligners (also referred to simply as aligners). However, embodiments also extend to other types of shells formed over molds, such as orthodontic retainers, orthodontic splints, sleep appliances for mouth insertion (e.g., for minimizing snoring, sleep apnea, etc.) and/or shells for non-dental applications. Accordingly, it should be understood that embodiments herein that refer to aligners also apply to other types of shells. For example, the principles, features and methods discussed may be applied to any application or process in which it is useful to perform image based quality control for any suitable type of shells that are form fitting devices such as eye glass frames, contact or glass lenses, hearing aids or plugs, artificial knee caps, prosthetic limbs and devices, orthopedic inserts, as well as protective equipment such as knee guards, athletic cups, or elbow, chin, and shin guards and other like athletic/protective devices.

The aligner 800 can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some cases, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 804 on teeth 802 with corresponding receptacles or apertures 806 in the appliance 800 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309, 215 and 6,830,450.

Figure 8B:
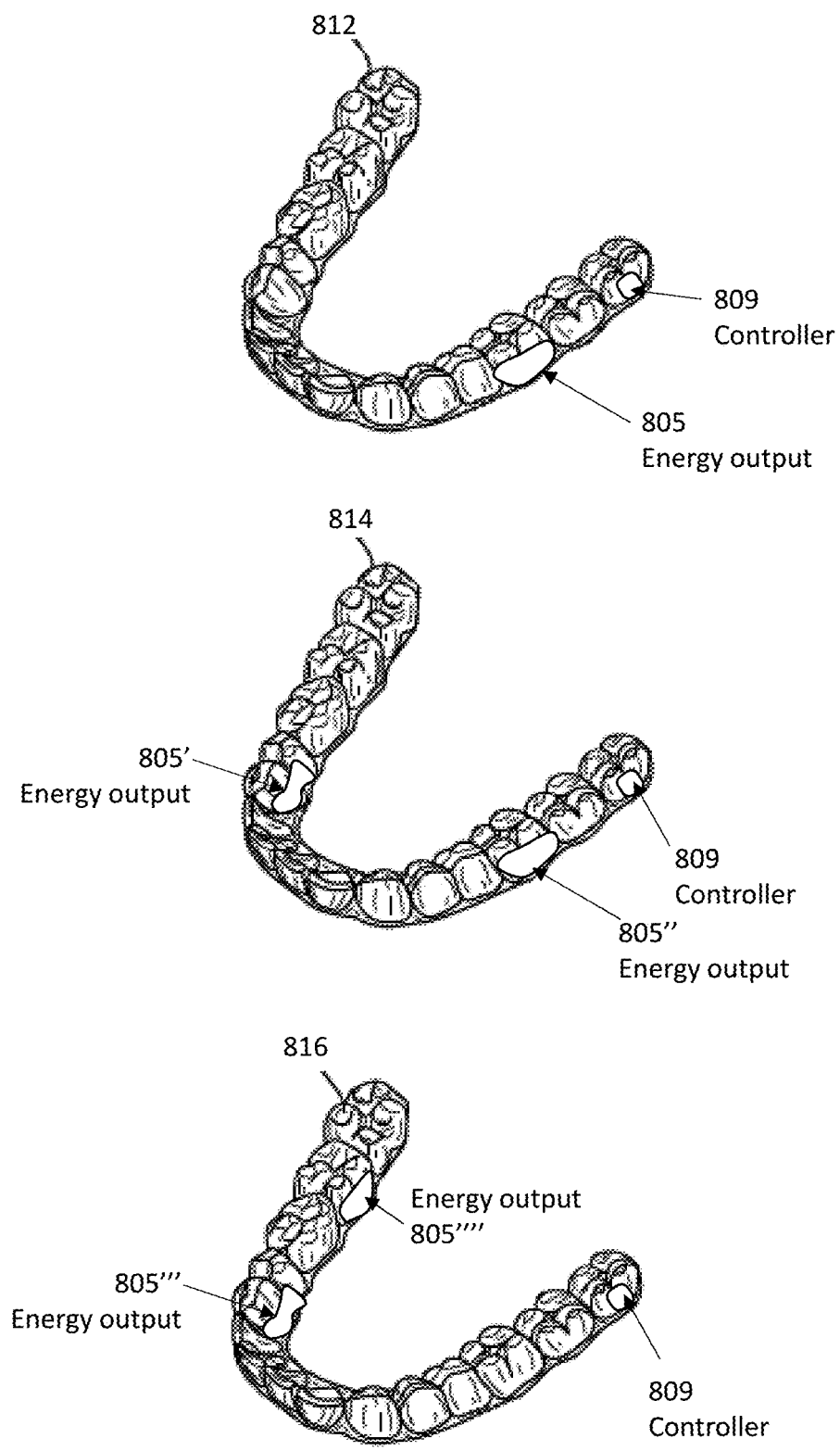
FIG. 8B illustrates a tooth repositioning system, in accordance with embodiments.

FIG. 8B illustrates a tooth repositioning system 810 including a plurality of appliances 812, 814, 816. As shown in FIG. 8B, each of the dental appliance in the tooth repositioning system 810 may include one or more energy outputs 805, 805', 805", 805''', 805'''', etc. and/or one or more controller(s) 809 to drive and regulate the application of energy. According to some embodiments, the heating elements function as resistive heating elements, as antennas that can be amped up by external radio frequency and controlled by, for example the etching on the dental appliance 800, and as shape memory alloys.

Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 810 can include a first appliance 812 corresponding to an initial tooth arrangement, one or more intermediate appliances 814 corresponding to one or more intermediate arrangements, and a final appliance 816 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

In some embodiments, the appliances 812, 814, 816 (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell.

In an example of indirect fabrication, a mold of a patient's dental arch may be fabricated from a digital model of the dental arch, and a shell may be formed over the mold (e.g., by thermoforming a polymeric sheet over the mold of the dental arch and then trimming the thermoformed polymeric sheet). The fabrication of the mold may be performed by a rapid prototyping machine (e.g., a stereolithography (SLA) 3D printer). The rapid prototyping machine may receive digital models of molds of dental arches and/or digital models of the appliances 812, 814, 816 after the digital models of the appliances 812, 814, 816 have been processed by processing logic of a computing device. The processing logic may include hardware (e.g., circuitry, dedicated logic, programmable logic, microcode, etc.), software (e.g., instructions executed by a processing device), firmware, or a combination thereof.

To manufacture the molds, a shape of a dental arch for a patient at a treatment stage is determined based on a treatment plan. In the example of orthodontics, the treatment plan may be generated based on an intraoral scan of a dental arch to be modeled. The intraoral scan of the patient's dental arch may be performed to generate a three dimensional (3D) virtual model of the patient's dental arch (mold). For example, a full scan of the mandibular and/or maxillary arches of a patient may be performed to generate 3D virtual models thereof. The intraoral scan may be performed by creating multiple overlapping intraoral images from different scanning stations and then stitching together the intraoral images to provide a composite 3D virtual model. In other applications, virtual 3D models may also be generated based on scans of an object to be modeled or based on use of computer aided drafting techniques (e.g., to design the virtual 3D mold). Alternatively, an initial negative mold may be generated from an actual object to be modeled (e.g., a dental impression or the like). The negative mold may then be scanned to determine a shape of a positive mold that will be produced.

Once the virtual 3D model of the patient's dental arch is generated, a dental practitioner may determine a desired treatment outcome, which includes final positions and orientations for the patient's teeth. Processing logic may then determine a number of treatment stages to cause the teeth to progress from starting positions and orientations to the target final positions and orientations. The shape of the final virtual 3D model and each intermediate virtual 3D model may be determined by computing the progression of tooth movement throughout orthodontic treatment from initial tooth placement and orientation to final corrected tooth placement and orientation. For each treatment stage, a separate virtual 3D model of the patient's dental arch at that treatment stage may be generated. The shape of each virtual 3D model will be different. The original virtual 3D model, the final virtual 3D model and each intermediate virtual 3D model is unique and customized to the patient.

Accordingly, multiple different virtual 3D models (digital designs) of a dental arch may be generated for a single patient. A first virtual 3D model may be a unique model of a patient's dental arch and/or teeth as they presently exist, and a final virtual 3D model may be a model of the patient's dental arch and/or teeth after correction of one or more teeth and/or a jaw. Multiple intermediate virtual 3D models may be modeled, each of which may be incrementally different from previous virtual 3D models.

Each virtual 3D model of a patient's dental arch may be used to generate a unique customized physical mold of the dental arch at a particular stage of treatment. The shape of the mold may be at least in part based on the shape of the virtual 3D model for that treatment stage. The virtual 3D model may be represented in a file such as a computer aided drafting (CAD) file or a 3D printable file such as a stereolithography (STL) file. The virtual 3D model for the mold may be sent to a third party (e.g., clinician office, laboratory, manufacturing facility or other entity). The virtual 3D model may include instructions that will control a fabrication system or device in order to produce the mold with specified geometries.

A clinician office, laboratory, manufacturing facility or other entity may receive the virtual 3D model of the mold, the digital model having been created as set forth above. The entity may input the digital model into a rapid prototyping machine. The rapid prototyping machine then manufactures the mold using the digital model. One example of a rapid prototyping manufacturing machine is a 3D printer. 3D printing includes any layer-based additive manufacturing processes. 3D printing may be achieved using an additive process, where successive layers of material are formed in proscribed shapes. 3D printing may be performed using extrusion deposition, granular materials binding, lamination, photopolymerization, continuous liquid interface production (CLIP), or other techniques. 3D printing may also be achieved using a subtractive process, such as milling.

In some instances, stereolithography (SLA), also known as optical fabrication solid imaging, is used to fabricate an SLA mold. In SLA, the mold is fabricated by successively printing thin layers of a photo-curable material (e.g., a polymeric resin) on top of one another. A platform rests in a bath of a liquid photopolymer or resin just below a surface of the bath. A light source (e.g., an ultraviolet laser) traces a pattern over the platform, curing the photopolymer where the light source is directed, to form a first layer of the mold. The platform is lowered incrementally, and the light source traces a new pattern over the platform to form another layer of the mold at each increment. This process repeats until the mold is completely fabricated. Once all of the layers of the mold are formed, the mold may be cleaned and cured.

Materials such as a polyester, a co-polyester, a polycarbonate, a polycarbonate, a thermopolymeric polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermopolymeric elastomer (TPE), a thermopolymeric vulcanizate (TPV) elastomer, a polyurethane elastomer, a block copolymer elastomer, a polyolefin blend elastomer, a thermopolymeric co-polyester elastomer, a thermopolymeric polyamide elastomer, or combinations thereof, may be used to directly form the mold. The materials used for fabrication of the mold can be provided in an uncured form (e.g., as a liquid, resin, powder, etc.) and can be cured (e.g., by photopolymerization, light curing, gas curing, laser curing, crosslinking, etc.). The properties of the material before curing may differ from the properties of the material after curing.

Appliances may be formed from each mold and when applied to the teeth of the patient, may provide forces to move the patient's teeth as dictated by the treatment plan. The shape of each appliance is unique and customized for a particular patient and a particular treatment stage. In an example, the appliances 812, 814, 816 can be pressure formed or thermoformed over the molds. Each mold may be used to fabricate an appliance that will apply forces to the patient's teeth at a particular stage of the orthodontic treatment. The appliances 812, 814, 816 each have teeth-receiving cavities that receive and resiliently reposition the teeth in accordance with a particular treatment stage.

In one embodiment, a sheet of material is pressure formed or thermoformed over the mold. The sheet may be, for example, a sheet of polymeric (e.g., an elastic thermopolymeric, a sheet of polymeric material, etc.). To thermoform the shell over the mold, the sheet of material may be heated to a temperature at which the sheet becomes pliable. Pressure may concurrently be applied to the sheet to form the now pliable sheet around the mold. Once the sheet cools, it will have a shape that conforms to the mold. In one embodiment, a release agent (e.g., a non-stick material) is applied to the mold before forming the shell. This may facilitate later removal of the mold from the shell. Forces may be applied to lift the appliance from the mold. In some instances, a breakage, warpage, or deformation may result from the removal forces. Accordingly, embodiments disclosed herein may determine where the probable point or points of damage may occur in a digital design of the appliance prior to manufacturing and may perform a corrective action.

Additional information may be added to the appliance. The additional information may be any information that pertains to the appliance. Examples of such additional information includes a part number identifier, patient name, a patient identifier, a case number, a sequence identifier (e.g., indicating which appliance a particular liner is in a treatment sequence), a date of manufacture, a clinician name, a logo and so forth. For example, after determining there is a probable point of damage in a digital design of an appliance, an indicator may be inserted into the digital design of the appliance. The indicator may represent a recommended place to begin removing the polymeric appliance to prevent the point of damage from manifesting during removal in some embodiments.

In some embodiments, a library of removal methods/patterns may be established and this library may be referenced when simulating the removal of the aligner in the numerical simulation. Different patients or production technicians may tend to remove aligners differently, and there might be a few typical patterns. For example: 1) some patients lift from the lingual side of posteriors first (first left and then right, or vice versa), and then go around the arch from left/right posterior section to the right/left posterior section; 2) similar to #1, but some other patients lift only one side of the posterior and then go around the arch; 3) similar to #1, but some patients lift from the buccal side rather than the lingual side of the posterior; 4) some patients lift from the anterior incisors and pull hard to remove the aligner; 5) some other patients grab both lingual and buccal side of a posterior location and pull out both sides at the same time; 6) some other patients grab a random tooth in the middle. The library can also include a removal guideline provided by the manufacturer of the aligner. Removal approach may also depend on presence or absence of attachments on teeth as some of the above method may result in more comfortable way of removal. Based on the attachment situation on each tooth, it can be determined how each patient would probably remove an aligner and adapt that removal procedure for that patient in that specific simulation.

After an appliance is formed over a mold for a treatment stage, that appliance is subsequently trimmed along a cutline (also referred to as a trim line) and the appliance may be removed from the mold. The processing logic may determine a cutline for the appliance. The determination of the cutline(s) may be made based on the virtual 3D model of the dental arch at a particular treatment stage, based on a virtual 3D model of the appliance to be formed over the dental arch, or a combination of a virtual 3D model of the dental arch and a virtual 3D model of the appliance. The location and shape of the cutline can be important to the functionality of the appliance (e.g., an ability of the appliance to apply desired forces to a patient's teeth) as well as the fit and comfort of the appliance. For shells such as orthodontic appliances, orthodontic retainers and orthodontic splints, the trimming of the shell may play a role in the efficacy of the shell for its intended purpose (e.g., aligning, retaining or positioning one or more teeth of a patient) as well as the fit of the shell on a patient's dental arch. For example, if too much of the shell is trimmed, then the shell may lose rigidity and an ability of the shell to exert force on a patient's teeth may be compromised. When too much of the shell is trimmed, the shell may become weaker at that location and may be a point of damage when a patient removes the shell from their teeth or when the shell is removed from the mold. In some embodiments, the cut line may be modified in the digital design of the appliance as one of the corrective actions taken when a probable point of damage is determined to exist in the digital design of the appliance.

On the other hand, if too little of the shell is trimmed, then portions of the shell may impinge on a patient's gums and cause discomfort, swelling, and/or other dental issues. Additionally, if too little of the shell is trimmed at a location, then the shell may be too rigid at that location. In some embodiments, the cutline may be a straight line across the appliance at the gingival line, below the gingival line, or above the gingival line. In some embodiments, the cutline may be a gingival cutline that represents an interface between an appliance and a patient's gingiva. In such embodiments, the cutline controls a distance between an edge of the appliance and a gum line or gingival surface of a patient.

Each patient has a unique dental arch with unique gingiva. Accordingly, the shape and position of the cutline may be unique and customized for each patient and for each stage of treatment. For instance, the cutline is customized to follow along the gum line (also referred to as the gingival line). In some embodiments, the cutline may be away from the gum line in some regions and on the gum line in other regions. For example, it may be desirable in some instances for the cutline to be away from the gum line (e.g., not touching the gum) where the shell will touch a tooth and on the gum line (e.g., touching the gum) in the interproximal regions between teeth. Accordingly, it is important that the shell be trimmed along a predetermined cutline.

In some embodiments, the orthodontic appliances herein (or portions thereof) can be produced using direct fabrication, such as additive manufacturing techniques (also referred to herein as "3D printing) or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can be categorized as follows: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances 812, 814, 816. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliances 812, 814, 816 can be directly fabricated using selective laser sintering. In some embodiments, selective laser sintering involves using a laser beam to selectively melt and fuse a layer of powdered material according to a desired cross-sectional shape in order to build up the object geometry. As yet another example, the appliances 812, 814, 816 can be directly fabricated by fused deposition modeling. In some embodiments, fused deposition modeling involves melting and selectively depositing a thin filament of thermoplastic polymer in a layer-by-layer manner in order to form an object. In yet another example, material jetting can be used to directly fabricate the appliances 812, 814, 816. In some embodiments, material jetting involves jetting or extruding one or more materials onto a build surface in order to form successive layers of the object geometry.

In some embodiments, the direct fabrication methods provided herein build up the object geometry in a layer-by-layer fashion, with successive layers being formed in discrete build steps. Alternatively or in combination, direct fabrication methods that allow for continuous build-up of an object geometry can be used, referred to herein as "continuous direct fabrication." Various types of continuous direct fabrication methods can be used. As an example, in some embodiments, the appliances 812, 814, 816 are fabricated using "continuous liquid interphase printing," in which an object is continuously built up from a reservoir of photopolymerizable resin by forming a gradient of partially cured resin between the building surface of the object and a polymerization-inhibited "dead zone." In some embodiments, a semi-permeable membrane is used to control transport of a photopolymerization inhibitor (e.g., oxygen) into the dead zone in order to form the polymerization gradient. Continuous liquid interphase printing can achieve fabrication speeds about 25 times to about 100 times faster than other direct fabrication methods, and speeds about 1000 times faster can be achieved with the incorporation of cooling systems. Continuous liquid interphase printing is described in U.S. Patent Publication Nos. 2015/0097315, 2015/0097316, and 2015/0102532, the disclosures of each of which are incorporated herein by reference in their entirety.

As another example, a continuous direct fabrication method can achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Such methods are described in U.S. Pat. No. 7,892,474, the disclosure of which is incorporated herein by reference in its entirety.

In another example, a continuous direct fabrication method can involve extruding a composite material composed of a curable liquid material surrounding a solid strand. The composite material can be extruded along a continuous three-dimensional path in order to form the object. Such methods are described in U.S. Patent Publication No. 2014/0061974, the disclosure of which is incorporated herein by reference in its entirety.

In yet another example, a continuous direct fabrication method utilizes a "heliolithography" approach in which the liquid photopolymer is cured with focused radiation while the build platform is continuously rotated and raised. Accordingly, the object geometry can be continuously built up along a spiral build path. Such methods are described in U.S. Patent Publication No. 2014/0265034, the disclosure of which is incorporated herein by reference in its entirety.

The direct fabrication approaches provided herein are compatible with a wide variety of materials, including but not limited to one or more of the following: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, a polytrimethylene terephthalate, a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, a thermoplastic polyamide elastomer, a thermoset material, or combinations thereof. The materials used for direct fabrication can be provided in an uncured form (e.g., as a liquid, resin, powder, etc.) and can be cured (e.g., by photopolymerization, light curing, gas curing, laser curing, crosslinking, etc.) in order to form an orthodontic appliance or a portion thereof. The properties of the material before curing may differ from the properties of the material after curing. Once cured, the materials herein can exhibit sufficient strength, stiffness, durability, biocompatibility, etc. for use in an orthodontic appliance. The post-curing properties of the materials used can be selected according to the desired properties for the corresponding portions of the appliance.

In some embodiments, relatively rigid portions of the orthodontic appliance can be formed via direct fabrication using one or more of the following materials: a polyester, a co-polyester, a polycarbonate, a thermoplastic polyurethane, a polypropylene, a polyethylene, a polypropylene and polyethylene copolymer, an acrylic, a cyclic block copolymer, a polyetheretherketone, a polyamide, a polyethylene terephthalate, a polybutylene terephthalate, a polyetherimide, a polyethersulfone, and/or a polytrimethylene terephthalate.

In some embodiments, relatively elastic portions of the orthodontic appliance can be formed via direct fabrication using one or more of the following materials: a styrenic block copolymer (SBC), a silicone rubber, an elastomeric alloy, a thermoplastic elastomer (TPE), a thermoplastic vulcanizate (TPV) elastomer, a polyurethane elastomer, a block copolymer elastomer, a polyolefin blend elastomer, a thermoplastic co-polyester elastomer, and/or a thermoplastic polyamide elastomer.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated before, during, and/or at the end of each build, and/or at predetermined time intervals (e.g., every nth build, once per hour, once per day, once per week, etc.), depending on the stability of the system. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

Optionally, the direct fabrication methods described herein allow for fabrication of an appliance including multiple materials, referred to herein as "multi-material direct fabrication." In some embodiments, a multi-material direct fabrication method involves concurrently forming an object from multiple materials in a single manufacturing step. For instance, a multi-tip extrusion apparatus can be used to selectively dispense multiple types of materials from distinct material supply sources in order to fabricate an object from a plurality of different materials. Such methods are described in U.S. Pat. No. 6,749,414, the disclosure of which is incorporated herein by reference in its entirety. Alternatively or in combination, a multi-material direct fabrication method can involve forming an object from multiple materials in a plurality of sequential manufacturing steps. For instance, a first portion of the object can be formed from a first material in accordance with any of the direct fabrication methods herein, then a second portion of the object can be formed from a second material in accordance with methods herein, and so on, until the entirety of the object has been formed.

Direct fabrication can provide various advantages compared to other manufacturing approaches. For instance, in contrast to indirect fabrication, direct fabrication permits production of an orthodontic appliance without utilizing any molds or templates for shaping the appliance, thus reducing the number of manufacturing steps involved and improving the resolution and accuracy of the final appliance geometry. Additionally, direct fabrication permits precise control over the three-dimensional geometry of the appliance, such as the appliance thickness. Complex structures and/or auxiliary components can be formed integrally as a single piece with the appliance shell in a single manufacturing step, rather than being added to the shell in a separate manufacturing step. In some embodiments, direct fabrication is used to produce appliance geometries that would be difficult to create using alternative manufacturing techniques, such as appliances with very small or fine features, complex geometric shapes, undercuts, interproximal structures, shells with variable thicknesses, and/or internal structures (e.g., for improving strength with reduced weight and material usage). For example, in some embodiments, the direct fabrication approaches herein permit fabrication of an orthodontic appliance with feature sizes of less than or equal to about 5 µm, or within a range from about 5 µm to about 50 µm, or within a range from about 20 µm to about 50 µm.

The direct fabrication techniques described herein can be used to produce appliances with substantially isotropic material properties, e.g., substantially the same or similar strengths along all directions. In some embodiments, the direct fabrication approaches herein permit production of an orthodontic appliance with a strength that varies by no more than about 25%, about 20%, about 15%, about 10%, about 5%, about 1%, or about 0.5% along all directions. Additionally, the direct fabrication approaches herein can be used to produce orthodontic appliances at a faster speed compared to other manufacturing techniques. In some embodiments, the direct fabrication approaches herein allow for production of an orthodontic appliance in a time interval less than or equal to about 1 hour, about 30 minutes, about 25 minutes, about 20 minutes, about 15 minutes, about 10 minutes, about 5 minutes, about 4 minutes, about 3 minutes, about 2 minutes, about 1 minutes, or about 30 seconds. Such manufacturing speeds allow for rapid "chair-side" production of customized appliances, e.g., during a routine appointment or checkup.

In some embodiments, the direct fabrication methods described herein implement process controls for various machine parameters of a direct fabrication system or device in order to ensure that the resultant appliances are fabricated with a high degree of precision. Such precision can be beneficial for ensuring accurate delivery of a desired force system to the teeth in order to effectively elicit tooth movements. Process controls can be implemented to account for process variability arising from multiple sources, such as the material properties, machine parameters, environmental variables, and/or post-processing parameters.

Material properties may vary depending on the properties of raw materials, purity of raw materials, and/or process variables during mixing of the raw materials. In many embodiments, resins or other materials for direct fabrication should be manufactured with tight process control to ensure little variability in photo-characteristics, material properties (e.g., viscosity, surface tension), physical properties (e.g., modulus, strength, elongation) and/or thermal properties (e.g., glass transition temperature, heat deflection temperature). Process control for a material manufacturing process can be achieved with screening of raw materials for physical properties and/or control of temperature, humidity, and/or other process parameters during the mixing process. By implementing process controls for the material manufacturing procedure, reduced variability of process parameters and more uniform material properties for each batch of material can be achieved. Residual variability in material properties can be compensated with process control on the machine, as discussed further herein.

Machine parameters can include curing parameters. For digital light processing (DLP)-based curing systems, curing parameters can include power, curing time, and/or grayscale of the full image. For laser-based curing systems, curing parameters can include power, speed, beam size, beam shape and/or power distribution of the beam. For printing systems, curing parameters can include material drop size, viscosity, and/or curing power. These machine parameters can be monitored and adjusted on a regular basis (e.g., some parameters at every 1-x layers and some parameters after each build) as part of the process control on the fabrication machine. Process control can be achieved by including a sensor on the machine that measures power and other beam parameters every layer or every few seconds and automatically adjusts them with a feedback loop. For DLP machines, gray scale can be measured and calibrated at the end of each build. In addition, material properties and/or photo-characteristics can be provided to the fabrication machine, and a machine process control module can use these parameters to adjust machine parameters (e.g., power, time, gray scale, etc.) to compensate for variability in material properties. By implementing process controls for the fabrication machine, reduced variability in appliance accuracy and residual stress can be achieved.

In many embodiments, environmental variables (e.g., temperature, humidity, Sunlight or exposure to other energy/curing source) are maintained in a tight range to reduce variable in appliance thickness and/or other properties. Optionally, machine parameters can be adjusted to compensate for environmental variables.

In many embodiments, post-processing of appliances includes cleaning, post-curing, and/or support removal processes. Relevant post-processing parameters can include purity of cleaning agent, cleaning pressure and/or temperature, cleaning time, post-curing energy and/or time, and/or consistency of support removal process. These parameters can be measured and adjusted as part of a process control scheme. In addition, appliance physical properties can be varied by modifying the post-processing parameters. Adjusting post-processing machine parameters can provide another way to compensate for variability in material properties and/or machine properties.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

Figure 8C:
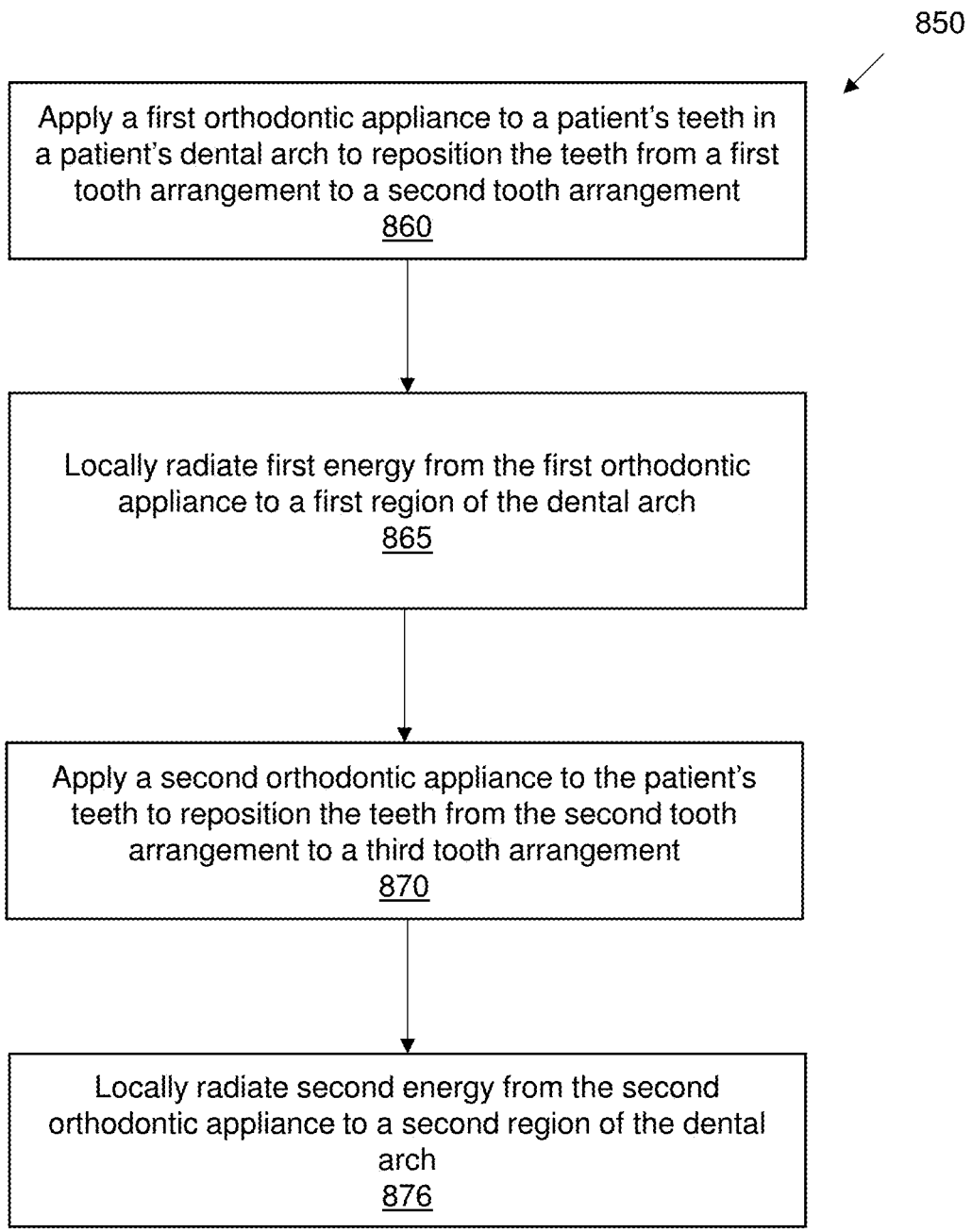
FIG. 8C illustrates a method of orthodontic treatment using a plurality of appliances, in accordance with embodiments.

FIG. 8C illustrates a method 850 of orthodontic treatment using a plurality of appliances, in accordance with embodiments. The method 850 can be practiced using any of the appliances or appliance sets described herein. In block 860, a first orthodontic appliance is applied to a patient's teeth in the patient's dental arch in order to reposition the teeth from a first tooth arrangement to a second tooth arrangement. As noted herein, the first orthodontic appliance may apply repositioning forces to a patient's crowns, roots, and/or other portions of the patient's teeth to move from a first tooth arrangement to a second tooth arrangement. The first orthodontic appliance may interact with one or more attachments on the patient's teeth to apply forces to the patient's teeth through those attachments.

In block 865, first energy is locally radiated from the first orthodontic appliance to a first region of the dental arch. The first region relate to a region that is to receive light energy as part of accelerated treatment and/or other therapy. The first energy may comprise light and/or heat. The first energy may include light energy, heat from housing elements, RF energy from radio waves, etc. The first energy may be locally radiated from an emitter coupled to and/or formed from a dental appliance. The first energy may be limited such that it has a first, more significant energy and/or intensity level in a specific area around the region of the dental arch and such that the light has a second, less significant energy and/or intensity level outside the specific area. A magnitude and/or distribution of the first energy may be such that the first energy falls below a specified level around the specific area.

In block 870, a second orthodontic appliance is applied to the patient's teeth in order to reposition the teeth from the second tooth arrangement to a third tooth arrangement. The second orthodontic appliance may apply repositioning forces to a patient's crowns, roots, and/or other portions of the patient's teeth to move from a second tooth arrangement to a third tooth arrangement. The second orthodontic appliance may interact with one or more attachments on the patient's teeth to apply forces to the patient's teeth through those attachments. In some variations, the attachments that the second orthodontic appliance interacts with may, but need not, be the same as the attachments the first orthodontic appliance interacts with.

In block 875, second energy is locally radiated from the second orthodontic appliance to a second region of the dental arch. The second region may, but need not, correspond to the first region and, as noted herein, may relate to a region that is to receive light energy as part of accelerated treatment and/or other therapy. The second energy may comprise light and/or heat. The second energy may include light energy, heat from housing elements, RF energy from radio waves, etc. The second energy may be locally radiated from an emitter coupled to and/or formed from a dental appliance. The second energy may be limited such that it has a first, more significant energy and/or intensity level in a specific area around the region of the dental arch and such that the light has a second, less significant energy and/or intensity level outside the specific area. A magnitude and/or distribution of the first energy may be such that the first energy falls below a specified level around the specific area. In various implementations, the second energy may (but need not) correspond in magnitude, direction, and/or other attributes to the first energy. In some implementations, the second energy is provided from a different emitter than the first energy was.

The method 850 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

Figure 9:
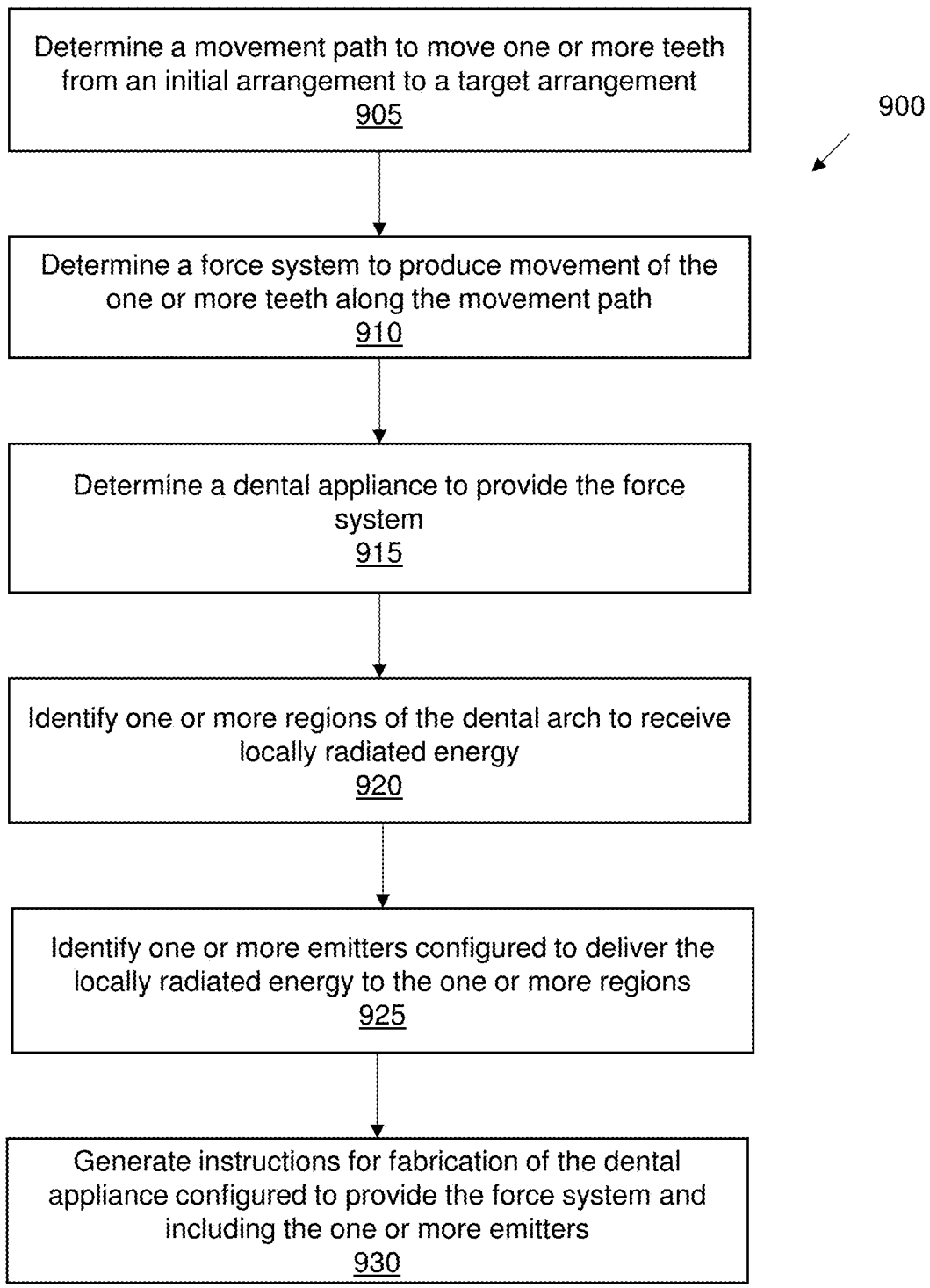
FIG. 9 illustrates a method for designing an orthodontic appliance, in accordance with embodiments.

FIG. 9 illustrates a method 900 for designing an orthodontic appliance to be produced by direct fabrication, in accordance with embodiments. The method 900 can be applied to any embodiment of the orthodontic appliances described herein. Some or all of the blocks of the method 900 can be performed by any suitable data processing system or device, e.g., one or more processors configured with suitable instructions.

In block 905, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In block 910, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

The determination of the force system can include constraints on the allowable forces, such as allowable directions and magnitudes, as well as desired motions to be brought about by the applied forces. For example, in fabricating palatal expanders, different movement strategies may be desired for different patients. For example, the amount of force needed to separate the palate can depend on the age of the patient, as very young patients may not have a fully-formed suture. Thus, in juvenile patients and others without fully-closed palatal sutures, palatal expansion can be accomplished with lower force magnitudes. Slower palatal movement can also aid in growing bone to fill the expanding suture. For other patients, a more rapid expansion may be desired, which can be achieved by applying larger forces. These requirements can be incorporated as needed to choose the structure and materials of appliances; for example, by choosing palatal expanders capable of applying large forces for rupturing the palatal suture and/or causing rapid expansion of the palate. Subsequent appliance stages can be designed to apply different amounts of force, such as first applying a large force to break the suture, and then applying smaller forces to keep the suture separated or gradually expand the palate and/or arch.

The determination of the force system can also include modeling of the facial structure of the patient, such as the skeletal structure of the jaw and palate. Scan data of the palate and arch, such as Xray data or 3D optical scanning data, for example, can be used to determine parameters of the skeletal and muscular system of the patient's mouth, so as to determine forces sufficient to provide a desired expansion of the palate and/or arch. In some embodiments, the thickness and/or density of the mid-palatal suture may be measured, or input by a treating professional. In other embodiments, the treating professional can select an appropriate treatment based on physiological characteristics of the patient. For example, the properties of the palate may also be estimated based on factors such as the patient's age—for example, young juvenile patients will typically require lower forces to expand the suture than older patients, as the suture has not yet fully formed.

In block 915, an orthodontic appliance configured to produce the force system is determined. Determination of the orthodontic appliance, appliance geometry, material composition, and/or properties can be performed using a treatment or force application simulation environment. A simulation environment can include, e.g., computer modeling systems, biomechanical systems or apparatus, and the like. Optionally, digital models of the appliance and/or teeth can be produced, such as finite element models. The finite element models can be created using computer program application software available from a variety of vendors. For creating solid geometry models, computer aided engineering (CAE) or computer aided design (CAD) programs can be used, such as the AutoCAD® software products available from Autodesk, Inc., of San Rafael, CA. For creating finite element models and analyzing them, program products from a number of vendors can be used, including finite element analysis packages from ANSYS, Inc., of Canonsburg, PA, and SIMULIA(Abaqus) software products from Dassault Systèmes of Waltham, MA.

Optionally, one or more orthodontic appliances can be selected for testing or force modeling. As noted above, a desired tooth movement, as well as a force system required or desired for eliciting the desired tooth movement, can be identified. Using the simulation environment, a candidate orthodontic appliance can be analyzed or modeled for determination of an actual force system resulting from use of the candidate appliance. One or more modifications can optionally be made to a candidate appliance, and force modeling can be further analyzed as described, e.g., in order to iteratively determine an appliance design that produces the desired force system.

In block 920, one or more regions of the dental arch to receive locally radiated light energy are determined. Portions of gums, teeth, and/or other dental arch may be identified for locally radiated energy. The one or more regions of the dental arch may comprise regions for which energy may accelerate orthodontic treatment (e.g., portions of the dental arch that are more susceptible to move due to application of energy). The one or more regions of the dental arch may include regions for which energy would be therapeutic. The one or more regions may correspond to the properties of regions described further herein.

In block 925, one or more emitters configured to deliver the locally radiated energy to the one or more regions are identified. The emitters may comprise discrete and/or integrated emitter components (LEDs, heaters, etc.). The emitters may also comprise portions integrally formed into an orthodontic appliance that are configured to provide locally radiated energy. Magnitude(s), intensity(ies), direction(s), types of energy (light, RF waves, heat, etc.) and/or other attributes of energy emitted from the emitters may be determined so that the locally radiated energy is at a first value in the regions one or more regions of the dental arch that are to receive locally radiated light, and at a second value outside the one or more regions. As noted herein, the second value may comprise a less significant value than the first value.

In block 930, instructions for fabrication of the orthodontic appliance incorporating the emitters are generated. The instructions can be configured to control a fabrication system or device in order to produce the orthodontic appliance with the specified orthodontic appliance. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.), in accordance with the various methods presented herein. In some embodiments, the instructions can be configured for indirect fabrication of the appliance, e.g., by thermoforming.

Method 900 may comprise additional blocks: 1) The upper arch and palate of the patient is scanned intraorally to generate three dimensional data of the palate and upper arch; 2) The three dimensional shape profile of the appliance is determined to provide a gap and teeth engagement structures as described herein.

Although the above blocks show a method 900 of designing an orthodontic appliance in accordance with some embodiments, a person of ordinary skill in the art will recognize some variations based on the teaching described herein. Some of the blocks may comprise sub-blocks. Some of the blocks may be repeated as often as desired. One or more blocks of the method 900 may be performed with any suitable fabrication system or device, such as the embodiments described herein. Some of the blocks may be optional, and the order of the blocks can be varied as desired.

Figure 10:
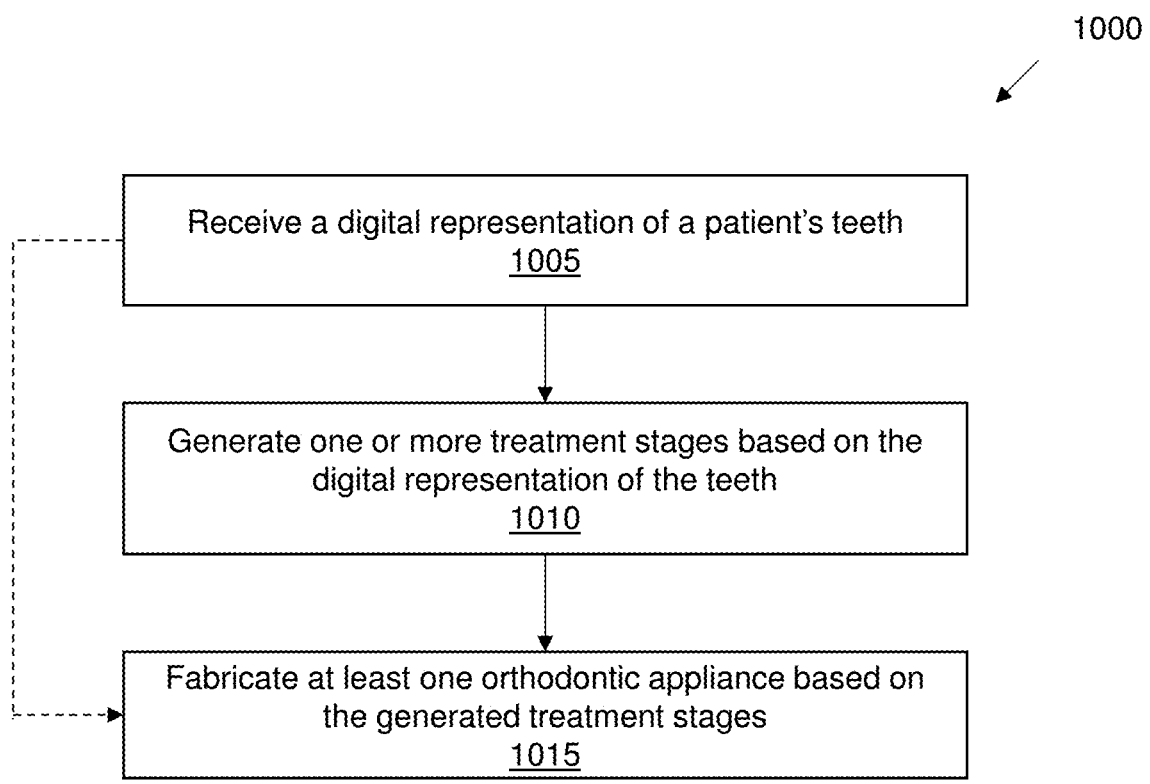
FIG. 10 illustrates a method for digitally planning an orthodontic treatment, in accordance with embodiments.

FIG. 10 illustrates a method 1000 for digitally planning an orthodontic treatment and/or design or fabrication of an appliance, in accordance with embodiments. The method 1700 can be applied to any of the treatment procedures described herein and can be performed by any suitable data processing system.

In block 1005, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In block 1010, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria. The treatment stages may include one or more areas to receive locally radiated light energy, as discussed further herein.

In block 1015, at least one orthodontic appliance is fabricated based on the generated treatment stages. For example, a set of appliances can be fabricated, each shaped according a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 10, design and/or fabrication of an orthodontic appliance, and perhaps a particular orthodontic treatment, may include use of a representation of the patient's teeth (e.g., receive a digital representation of the patient's teeth 1005), followed by design and/or fabrication of an orthodontic appliance based on a representation of the patient's teeth in the arrangement represented by the received representation.

Although various illustrative embodiments are described, any of a number of changes may be made to various embodiments without departing from the scope of the invention as described by the claims. For example, the order in which various described method steps are performed may often be changed in alternative embodiments, and in other alternative embodiments, one or more method steps may be skipped altogether. Optional features of various device and system embodiments may be included in some embodiments and not in others. Therefore, the foregoing description is provided primarily for example purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure covers all adaptations or variations of various embodiments. Combinations of the above embodiments, and other embodiments not specifically described herein, will be apparent to those of skill in the art upon reviewing the above description.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the example term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for example purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An aligner system comprising a sequence of aligners for treating a dental arch according to a treatment plan, the aligner system comprising:
   a first aligner of the sequence of aligners, the first aligner comprising:
      a first polymer shell comprising first teeth receiving cavities configured to fit on the dental arch having a first initial tooth arrangement according to a first stage of the treatment plan, the first teeth receiving cavities having a geometry corresponding to a first target tooth arrangement according to the first stage of the treatment plan, the first target tooth arrangement being different than the first initial tooth arrangement, wherein the first polymer shell has a shape that is customized to apply a first local force to a first region of the dental arch to move one or more first teeth of the dental arch from the first initial tooth arrangement toward the first target tooth arrangement according to the first stage of the treatment plan; and
      a first controller configured to cause a first heating element to emit heat energy from a first heat output region of the first polymer shell according to a first predetermined heating profile, wherein the first heat output region is arranged to heat a first target region of the dental arch that is associated with moving the one or more first teeth of the dental arch, wherein the heat energy from the first heat output region has a first dose to interact with tissue associated with the one or more first teeth to improve an outcome of the first stage of the treatment plan; and
   a second aligner of the sequence of aligners, the second aligner comprising:
      a second polymer shell comprising second teeth receiving cavities configured to fit on the dental arch having a second initial tooth arrangement according to a second stage of the treatment plan, the second teeth receiving cavities having a geometry corresponding to a second target tooth arrangement according to the second stage of the treatment plan, the second target tooth arrangement being different than the second initial tooth arrangement, wherein the second polymer shell has a shape that is customized to apply a second local force to a second region of the dental arch to move one or more second teeth of the dental arch from the second initial tooth arrangement toward the second target tooth arrangement according to the second stage of the treatment plan; and
      a second controller configured to cause a second heating element to emit heat energy from a second heat output region of the second polymer shell according to a second predetermined heating profile, wherein the second heat output region is arranged to heat a second target region of the dental arch that is associated with moving the one or more second teeth of the dental arch, the one or more second teeth being different from the one or more first teeth, wherein the heat energy from the second heat output region has a second dose to interact with tissue associated with the one or more second teeth to improve an outcome of the second stage of the treatment plan;
      wherein the second aligner is after the first aligner in the sequence of aligners.

2. The aligner system of claim 1, wherein:
   each of the first and second heat output regions is bounded by material having a lower thermal conductance than respective first and second heat output regions.

3. The aligner system of claim 1, wherein the first and second heat output regions are positioned to emit the heat energy along an edge region between a tooth-contacting side and an outer side of the corresponding first or second teeth receiving cavities, wherein the tooth-contacting side is arranged to contact teeth of the dental arch when worn on the dental arch, and wherein the outer side is arrange not to contact the teeth of the dental arch when worn on the dental arch.

4. The aligner system of claim 1, wherein each of the first and second heating elements is arranged to deliver the respective heat energy to one or more of: the teeth, gingiva, and palate of the patient.

5. The aligner system of claim 1, wherein each of the first and second heat output regions is configured to emit the respective heat energy from a lingual side of corresponding first and second teeth receiving cavities.

6. The aligner system of claim 1, wherein each of the first and second regions of the dental arch comprises a subset of the dental arch.

7. The aligner system of claim 1, wherein the one or more first and second teeth include at least one tooth in common.

8. The aligner system of claim 1, wherein each of the first and second aligners is configured to regulate emission of the heat energy one or more times per day depending on the day of the week.

9. The aligner system of claim 1, wherein each of the first and second aligners is configured to regulate a duration of emitting the heat energy.

10. The aligner system of claim 1, wherein each of the first and second aligners is configured to regulate emission of the heat energy to multiple times in the day.

11. The aligner system of claim 1, wherein each of the first and second aligners is configured to control timing of the heat energy based on whether the time of day is one or more of: nighttime, daytime, morning, and evening.

12. The aligner system of claim 1, wherein each of the first and second aligners is configured to emit the heat energy for a respective customized first or second emission duration that is determined based on the treatment plan, wherein the first heat output region is configured to emit the first predetermined heating profile for a first emission duration and the second heat output region is configured to emit the second predetermined heating profile for a second emission duration that is different than the first emission duration.

13. The aligner system of claim 1, wherein each of the first and second aligners is configured to limit an amount of heat energy delivered to the respective one or more first or second teeth.

14. The aligner system of claim 13, wherein the first aligner is configured to limit the amount of heat energy delivered to the one or more first teeth to a first amount of heat energy, and the second aligner is configured to limit the amount of heat energy delivered to the one or more second teeth to a second amount of heat energy that is different than the first amount of heat energy.

15. The aligner system of claim 1, wherein the first controller is configured for feedback control of a first temperature of the first heat output region, and the second controller is configured for feedback control of a second temperature of the second heat output region.

16. The aligner system of claim 15, wherein the first aligner includes a first thermistor configured for feedback to the first controller, and the second aligner includes a second thermistor configured for feedback to the second controller.

17. The aligner system of claim 1, wherein a material of the first and second heat output regions have a higher thermal conductance than a material of adjacent regions of respective first and second polymer shells.

18. The aligner system of claim 1, wherein each of the first and second controllers is configured to cause the corresponding first or second heating element to deliver the dose of the heat energy based on sensed data, wherein the sensed data comprises one or more of: movement, jaw position, tooth position, force or pressure on the corresponding one or more first or second teeth.

19. An orthodontic aligner system comprising a sequence of aligners for treating a dental arch according to a treatment plan, the orthodontic aligner system comprising:
a first aligner of the sequence of aligners, the first aligner comprising:
a first polymer shell comprising first teeth receiving cavities configured to fit on the dental arch having an first initial tooth arrangement, the first teeth receiving cavities having a geometry corresponding to a first target tooth arrangement according to a first stage of the treatment plan, the first target tooth arrangement being different than the first initial tooth arrangement, wherein the first polymer shell has a shape that is customized to apply a first local force to a first region of the dental arch to move one or more first teeth of the dental arch from the first initial tooth arrangement toward the first target tooth arrangement according to the first stage of the treatment plan; and
a first controller configured to cause a first heating element to emit heat energy from a first heat output region of the first polymer shell according to a first predetermined heating profile, wherein the first heat output region is arranged to heat a first target region of the dental arch for moving the one or more first teeth of the dental arch, wherein the heat energy from the first heat output region has a first dose to interact with tissue associated with the one or more first teeth to improve an outcome of the first stage of the treatment plan, and wherein the first controller is configured for feedback control of a temperature of the first heat output region; and
a second aligner of the sequence of aligners, the second aligner comprising:
a second polymer shell comprising second teeth receiving cavities configured to fit on the dental arch having a second initial tooth arrangement, the second teeth receiving cavities having a geometry corresponding to a second target tooth arrangement according to a second stage of the treatment plan, the second target tooth arrangement being different than the second initial tooth arrangement, wherein the second polymer shell has a shape that is customized to apply a second local force to a second region of the dental arch to move one or more second teeth of the dental arch from the second initial tooth arrangement toward the second target tooth arrangement according to the second stage of the treatment plan; and
a second controller configured to cause a second heating element to emit heat energy from a second heat output region of the second polymer shell according to a second predetermined heating profile, wherein the second heat output region is arranged to heat a second target region of the dental arch for moving the one or more second teeth of the dental arch, the one or more second teeth different from the one or more first teeth, wherein the heat energy from the second heat output region has a second dose to interact with tissue associated with the one or more second teeth to improve an outcome of the second stage of the treatment plan, and wherein the second controller is configured for feedback control of a temperature of the second heat output region
wherein the second aligner is after the first aligner in the sequence of aligners.

20. The orthodontic aligner system of claim 19, wherein each of the first and second aligners is configured to prevent the heat energy from being emitted from regions adjacent to the corresponding first or second heat output region.

21. The orthodontic aligner system of claim 19, wherein each of the first and second heating elements is configured to emit the heat energy along an edge of the corresponding first or second polymer shell.

22. The orthodontic aligner system of claim 19, wherein each of the first and second controllers is configured to cause the corresponding first or second heating element to deliver the dose of the heat energy based on sensed data.

23. The orthodontic aligner system of claim 22, wherein the sensed data comprises one or more of: movement, jaw position, tooth position, force or pressure on the corresponding one or more first or second teeth.

24. The orthodontic aligner system of claim 19, wherein each of the first and second heat output regions is positioned on buccal side of the corresponding first or second polymer shell.

25. The orthodontic aligner system of claim 19, wherein each of the first and second heat output regions is positioned in a molar region of the corresponding first or second polymer shell.

26. The orthodontic aligner system of claim 19, wherein each of the first and second heat output regions is on a lingual side, a buccal side, or a lingual side and a buccal side of the corresponding first or second polymer shell.

27. The orthodontic aligner system of claim 19, wherein the first aligner includes a first thermistor configured for feedback to the first controller, and the second aligner includes a second thermistor configured for feedback to the second controller.

28. The orthodontic aligner system of claim 19, wherein a material of the first and second heat output regions have a higher thermal conductance than a material of adjacent regions of respective first and second polymer shells.

29. A method of orthodontically repositioning a patient's teeth using a sequence of aligners for treating the patient's teeth according to a treatment plan, the method comprising:
positioning a first aligner of the sequence of aligners on a patient's dental arch to apply a first local force to a first region of the patient's dental arch to move one or more first teeth of the patient's dental arch, wherein the first aligner comprises a first polymer shell including first teeth receiving cavities configured to fit on the patient's dental arch having an initial tooth arrangement, the first teeth receiving cavities having a geometry corresponding to a first target tooth arrangement according to a first stage of the treatment plan, the first target tooth arrangement being different than the initial tooth arrangement, and wherein the first polymer shell has a shape that is customized to apply the first local force to move the one or more first teeth of the patient's dental arch from the initial tooth arrangement toward the first target tooth arrangement according to the first stage of the treatment plan;
causing, by a first controller, a first heating element to emit heat energy from a first heat output region of the first aligner according to a first predetermined heating profile, wherein the first heat output region is arranged to heat a first target region of the patient's dental arch that is associated with moving the one or more first teeth of the patient's dental arch, wherein the heat energy applied from the first heat output region has a first dose to interact with tissue associated with the one or more first teeth to improve an outcome of the first stage of the treatment plan;
positioning a second aligner of the sequence of aligners on the patient's dental arch to apply a second local force to a second region of the patient's dental arch to move one or more second teeth of the patient's dental arch, the one or more second teeth different than the one or more first teeth wherein the second aligner comprises a second polymer shell including second teeth receiving cavities configured to fit on the patient's dental arch, the second teeth receiving cavities having a geometry corresponding to a second target tooth arrangement according to a second stage of the treatment plan, the second target tooth arrangement being different than the first target tooth arrangement, wherein the second polymer shell has a shape that is customized to apply the second local force to move the one or more second teeth of the patient's dental arch from the first target tooth arrangement toward the second target tooth arrangement according to the second stage of the treatment plan; and
causing, by a second controller, a second heating element to emit heat energy from a second heat output region of the second aligner according to a second predetermined heating profile, wherein the first heat output region is arranged to heat a second target region of the patient's dental arch that is associated with moving the one or more second teeth of the patient's dental arch, wherein the heat energy applied from the second heat output region has a second dose to interact with tissue associated with the one or more second teeth to improve an outcome of the second stage of the treatment plan;
wherein the second aligner is after the first aligner in the sequence of aligners.

30. The method of claim 29, wherein emitting the heat energy from each of the first and second aligners comprises emitting the heat energy from the respective first or second heating element that is integral to the respective first and second aligners.

31. The method of claim 29, wherein emitting the heat energy from each the first and second aligners comprises emitting the heat energy for a predetermined dose while the patient is wearing each of the first and second aligners.

32. The method of claim 29, wherein emitting the heat energy from each the first and second aligners comprises emitting the heat energy based on data from a sensor on each of the first and second aligners.

33. The method of claim 29, wherein emitting the heat energy comprises emitting the heat energy when the patient's mouth is closed.

34. The method of claim 29, wherein the first controller receives feedback of a first temperature of the first heat output region, and the second controller receives feedback of a second temperature of the second heat output region.

35. The method of claim 34, wherein the first aligner includes a first thermistor configured for feedback to the first controller, and the second aligner includes a second thermistor configured for feedback to the second controller.

36. The method of claim 29, wherein a material of the first and second heat output regions have a higher thermal conductance than a material of adjacent regions of respective first and second polymer shells.

37. The method of claim 29, wherein each of the first and second heating elements emit the heat energy along an edge of the corresponding first or second polymer shell.

38. The method of claim 29, wherein each of the first and second controllers cause the corresponding first or second heating element to deliver the dose of the heat energy based on sensed data, wherein the sensed data comprises one or more of: movement, jaw position, tooth position, force or pressure on the corresponding one or more first or second teeth.

* * * * *